(12) United States Patent
Thomas et al.

(10) Patent No.: US 7,670,141 B2
(45) Date of Patent: Mar. 2, 2010

(54) ORAL IRRIGATOR

(75) Inventors: Brenda Lee Thomas, Windsor, CO (US); Kurt Michael Taylor, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 381 days.

(21) Appl. No.: 11/483,376

(22) Filed: Jul. 7, 2006

(65) Prior Publication Data

US 2008/0008979 A1    Jan. 10, 2008

(51) Int. Cl.
*A61C 17/02* (2006.01)
(52) U.S. Cl. .............................. 433/80; 433/85; 433/88; 433/100
(58) Field of Classification Search ............. 433/80–85, 433/87–89, 98–100; 222/360, 361, 394; 137/625, 625.35, 625.38, 625.4, 625.48, 137/595, 862; 251/325, 398; 604/30, 33, 604/118, 119, 121, 125, 146, 249, 537
See application file for complete search history.

(56) References Cited

U.S. PATENT DOCUMENTS

| | | | |
|---|---|---|---|
| 555,588 A | 3/1896 | Spencer | |
| 1,278,225 A | 9/1918 | Schamberg | |
| 1,498,267 A | 6/1924 | Hachman | |
| 1,650,686 A * | 11/1927 | Binks | ................. 239/414 |
| 1,681,320 A | 8/1928 | Bergl et al. | |
| 1,933,454 A | 10/1933 | Sidney | |
| 2,669,233 A * | 2/1954 | Friend | ................. 604/33 |
| 2,783,919 A | 3/1957 | Ansell | |
| 2,794,437 A | 6/1957 | Tash | |
| 2,984,452 A | 5/1961 | Hooper | |
| 3,089,490 A | 5/1963 | Goldberg | |
| 3,096,913 A | 7/1963 | Jousson | |
| 3,144,867 A | 8/1964 | Trupp et al. | |
| 3,209,956 A | 10/1965 | McKenzie | |
| 3,216,619 A | 11/1965 | Richards et al. | |
| 3,225,759 A | 12/1965 | Drapen et al. | |
| 3,227,158 A | 1/1966 | Mattingly | |

(Continued)

FOREIGN PATENT DOCUMENTS

CA    851479    9/1970

(Continued)

OTHER PUBLICATIONS

Non-Final Office Action, U.S. Appl. No. 10/749,675, 16 pages, Jun. 8, 2005.

(Continued)

*Primary Examiner*—Cris L Rodriguez
*Assistant Examiner*—Michael R Ballinger
(74) *Attorney, Agent, or Firm*—Dorsey & Whitney LLP

(57) ABSTRACT

The present invention is an oral irrigator comprising a pump, a discharge nozzle and a pressure control. The pump has a generally constant operating speed and feeds the discharge nozzle. The pressure control is adapted to modify a discharge pressure at the nozzle without a significant change in pump speed. The pressure control modifies a level of fluid flow restriction between the pump and the nozzle. The modification of the level of fluid flow restriction is accomplished by modifying aspects of a fluid flow path extending through the pressure control. The aspects modified include the diameter, length and/or number of direction changes of the fluid flow path.

21 Claims, 28 Drawing Sheets

U.S. PATENT DOCUMENTS

| | | |
|---|---|---|
| 3,297,558 A | 1/1967 | Hillquist |
| D208,778 S | 10/1967 | Koch |
| D209,395 S | 11/1967 | Gilbert |
| 3,370,214 A | 2/1968 | Aymar |
| 3,391,696 A | 7/1968 | Woodward |
| 3,400,999 A | 9/1968 | Goldstein |
| 3,418,552 A | 12/1968 | Holmes |
| 3,420,228 A | 1/1969 | Kalbfeld |
| 3,453,969 A | 7/1969 | Mattingly |
| 3,465,751 A | 9/1969 | Powers |
| 3,487,828 A | 1/1970 | Troy |
| 3,496,933 A | 2/1970 | Lloyd |
| 3,499,440 A | 3/1970 | Gibbs |
| 3,501,203 A | 3/1970 | Falk |
| 3,502,072 A | 3/1970 | Stillman |
| 3,517,669 A * | 6/1970 | Buono et al. ............... 604/119 |
| D218,270 S | 8/1970 | Soper |
| 3,522,801 A | 8/1970 | Robinson |
| 3,536,065 A | 10/1970 | Moret |
| 3,537,444 A | 11/1970 | Garn |
| 3,547,110 A | 12/1970 | Balamuth |
| 3,572,375 A | 3/1971 | Rosenberg |
| 3,578,884 A | 5/1971 | Jacobson |
| 3,583,609 A | 6/1971 | Oppenheimer |
| 3,590,813 A | 7/1971 | Roszyk |
| 3,608,548 A | 9/1971 | Lewis |
| 3,636,947 A | 1/1972 | Balamuth |
| 3,651,576 A | 3/1972 | Massa |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,977 A | 5/1974 | Balamuth et al. |
| 3,827,147 A | 8/1974 | Condon |
| 3,840,795 A | 10/1974 | Roszyk et al. |
| 3,854,209 A | 12/1974 | Franklin et al. |
| 3,874,506 A | 4/1975 | Hill et al. |
| 3,912,125 A | 10/1975 | Acklin |
| 3,943,628 A | 3/1976 | Kronman et al. |
| 3,973,558 A | 8/1976 | Stouffer et al. |
| 4,001,526 A | 1/1977 | Olson |
| 4,004,302 A | 1/1977 | Hori |
| 4,007,739 A | 2/1977 | Bron et al. |
| 4,040,675 A * | 8/1977 | Richmond et al. ............ 303/89 |
| D246,667 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,108,167 A | 8/1978 | Hickman et al. |
| 4,108,178 A | 8/1978 | Betush |
| 4,109,650 A | 8/1978 | Peclard |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,182,038 A | 1/1980 | Fleer |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| 4,248,589 A | 2/1981 | Lewis |
| 4,249,899 A | 2/1981 | Davis |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,412,823 A | 11/1983 | Sakai et al. |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A * | 11/1985 | Kinoshita ................ 600/158 |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A * | 9/1986 | Schulze ...................... 239/1 |
| 4,619,612 A | 10/1986 | Weber et al. |
| 4,629,425 A | 12/1986 | Detsch |
| 4,636,198 A | 1/1987 | Stade |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,770,632 A | 9/1988 | Ryder et al. |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,450 A * | 5/1990 | Imonti et al. ............... 604/240 |
| 4,928,675 A | 5/1990 | Thornton |
| 4,930,660 A | 6/1990 | Porteous |
| 4,941,459 A | 7/1990 | Mathur |

| | | | | | | |
|---|---|---|---|---|---|---|
| 4,950,159 A | 8/1990 | Hansen | | 5,470,305 A | 11/1995 | Arnett et al. |
| 4,958,629 A | 9/1990 | Peace et al. | | 5,474,450 A | 12/1995 | Chronister |
| 4,958,751 A | 9/1990 | Curtis et al. | | 5,474,451 A | 12/1995 | Dalrymple et al. |
| 4,961,698 A | 10/1990 | Vlock | | 5,484,281 A | 1/1996 | Renow et al. |
| 4,966,551 A * | 10/1990 | Betush ............. 433/95 | | 5,487,877 A | 1/1996 | Choi |
| 4,969,874 A | 11/1990 | Michel et al. | | 5,490,779 A | 2/1996 | Malmin |
| 4,973,247 A | 11/1990 | Varnes et al. | | D369,656 S | 5/1996 | Vos |
| 4,973,250 A | 11/1990 | Milman | | 5,525,058 A | 6/1996 | Gallant et al. |
| 4,975,054 A | 12/1990 | Esrock | | 5,526,841 A | 6/1996 | Detsch et al. |
| 4,979,503 A * | 12/1990 | Chernack ............. 601/165 | | 5,540,587 A | 7/1996 | Malmin |
| 4,979,504 A | 12/1990 | Mills | | 5,547,374 A | 8/1996 | Coleman |
| 4,989,590 A | 2/1991 | Baum et al. | | D373,631 S | 9/1996 | Maeda et al. |
| 4,998,880 A | 3/1991 | Nerli | | 5,554,025 A | 9/1996 | Kinsel |
| 5,013,241 A | 5/1991 | Von Gutfeld et al. | | 5,616,028 A * | 4/1997 | Hafele et al. ............. 433/80 |
| 5,019,054 A * | 5/1991 | Clement et al. ............. 604/248 | | 5,634,791 A | 6/1997 | Matsuura et al. |
| 5,027,798 A | 7/1991 | Primiano | | 5,636,987 A | 6/1997 | Serfaty |
| 5,029,576 A | 7/1991 | Evans, Sr. | | 5,640,735 A | 6/1997 | Manning |
| 5,033,961 A | 7/1991 | Kankler et al. | | 5,653,591 A | 8/1997 | Loge |
| D318,918 S | 8/1991 | Hartwein | | 5,667,483 A | 9/1997 | Santos |
| 5,049,071 A | 9/1991 | Davis et al. | | 5,697,784 A | 12/1997 | Hafele et al. |
| 5,060,825 A * | 10/1991 | Palmer et al. ............. 222/25 | | 5,709,545 A | 1/1998 | Johnston et al. |
| 5,064,168 A * | 11/1991 | Raines et al. ............. 251/322 | | 5,716,007 A | 2/1998 | Nottingham et al. |
| 5,082,443 A | 1/1992 | Lohn | | 5,749,726 A | 5/1998 | Kinsel |
| 5,086,756 A | 2/1992 | Powell | | 5,851,079 A * | 12/1998 | Horstman et al. ............. 401/174 |
| 5,095,893 A | 3/1992 | Rawden, Jr. | | D403,511 S | 1/1999 | Serbinski |
| 5,098,291 A | 3/1992 | Curtis et al. | | D406,334 S | 3/1999 | Rosenthal et al. |
| 5,125,835 A | 6/1992 | Young | | 5,876,201 A | 3/1999 | Wilson et al. |
| 5,127,831 A | 7/1992 | Bab | | D413,975 S | 9/1999 | Maeda |
| 5,142,723 A | 9/1992 | Lustig et al. | | D417,082 S | 11/1999 | Classen et al. |
| 5,150,841 A | 9/1992 | Silvenis et al. | | 5,993,402 A | 11/1999 | Sauer et al. |
| 5,172,810 A | 12/1992 | Brewer | | 6,030,215 A | 2/2000 | Ellion et al. |
| 5,183,035 A | 2/1993 | Weir | | D425,615 S | 5/2000 | Bachman et al. |
| 5,197,458 A | 3/1993 | Ito et al. | | D425,981 S | 5/2000 | Bachman et al. |
| 5,197,460 A | 3/1993 | Ito et al. | | 6,056,710 A | 5/2000 | Bachman et al. |
| 5,199,871 A | 4/1993 | Young | | D426,633 S | 6/2000 | Bachman et al. |
| 5,203,697 A | 4/1993 | Malmin | | 6,124,699 A | 9/2000 | Suzuki et al. |
| 5,204,004 A | 4/1993 | Johnston et al. | | D434,500 S | 11/2000 | Pollock et al. |
| 5,208,933 A | 5/1993 | Lustig et al. | | 6,159,006 A | 12/2000 | Cook et al. |
| 5,218,956 A | 6/1993 | Handler et al. | | D435,905 S | 1/2001 | Bachman et al. |
| 5,220,914 A | 6/1993 | Thompson | | D439,781 S | 4/2001 | Spore |
| 5,228,646 A * | 7/1993 | Raines ............. 251/95 | | D441,861 S | 5/2001 | Hafliger |
| 5,230,624 A | 7/1993 | Wolf et al. | | 6,234,205 B1 * | 5/2001 | D'Amelio et al. ...... 137/625.17 |
| 5,232,687 A | 8/1993 | Geimer | | 6,247,929 B1 * | 6/2001 | Bachman et al. ............. 433/80 |
| 5,235,968 A | 8/1993 | Woog | | D449,884 S | 10/2001 | Tobin et al. |
| 5,246,367 A | 9/1993 | Ito et al. | | 6,475,173 B1 | 11/2002 | Bachman et al. |
| 5,252,064 A | 10/1993 | Baum et al. | | 6,497,572 B2 | 12/2002 | Hood et al. |
| 5,257,933 A | 11/1993 | Jousson | | D470,660 S | 2/2003 | Schaber |
| D341,943 S | 12/1993 | Si-Hoe | | D475,346 S | 6/2003 | McCurrach et al. |
| 5,267,586 A | 12/1993 | Jankavaara | | 6,632,091 B1 | 10/2003 | Cise et al. |
| 5,269,684 A | 12/1993 | Fischer | | D482,451 S | 11/2003 | Page et al. |
| 5,281,137 A | 1/1994 | Jousson | | 6,659,674 B2 | 12/2003 | Carlucci et al. |
| 5,281,139 A | 1/1994 | Frank et al. | | D486,573 S | 2/2004 | Callaghan et al. |
| 5,282,745 A | 2/1994 | Wiltrout et al. | | 6,689,078 B1 | 2/2004 | Rehkemper et al. |
| 5,286,192 A | 2/1994 | Dixon | | 6,699,208 B2 | 3/2004 | Bachman et al. |
| 5,286,201 A | 2/1994 | Yu | | 6,719,561 B2 | 4/2004 | Gugel et al. |
| 5,297,962 A | 3/1994 | O'Connor et al. | | D489,183 S | 5/2004 | Akahori et al. |
| D346,212 S | 4/1994 | Hosl | | 6,739,782 B1 | 5/2004 | Rehkemper et al. |
| 5,302,123 A | 4/1994 | Bechard | | D490,899 S | 6/2004 | Gagnon |
| 5,317,691 A | 5/1994 | Traeger | | D492,996 S | 7/2004 | Rehkemper et al. |
| 5,321,865 A | 6/1994 | Kaeser | | 6,766,549 B2 | 7/2004 | Klupt |
| 5,344,317 A | 9/1994 | Pacher et al. | | D495,142 S | 8/2004 | Berde |
| D351,892 S | 10/1994 | Wolf et al. | | D495,143 S | 8/2004 | Berde |
| 5,360,338 A | 11/1994 | Waggoner | | 6,779,216 B2 | 8/2004 | Davies et al. |
| 5,368,548 A | 11/1994 | Jousson | | 6,796,796 B2 | 9/2004 | Segal |
| 5,370,534 A | 12/1994 | Wolf et al. | | D499,885 S | 12/2004 | Xi |
| D354,168 S | 1/1995 | Hartwein | | 6,884,069 B2 | 4/2005 | Goldman |
| 5,378,149 A | 1/1995 | Stropko | | D509,585 S | 9/2005 | Kling et al. |
| 5,380,201 A | 1/1995 | Kawata | | D513,638 S | 1/2006 | Pan |
| D356,864 S | 3/1995 | Woog | | D530,010 S | 10/2006 | Luettgen et al. |
| 5,399,089 A | 3/1995 | Eichman et al. | | D533,720 S | 12/2006 | Vu |
| D358,883 S | 5/1995 | Vos | | D565,175 S | 3/2008 | Boyd et al. |
| 5,456,672 A | 10/1995 | Diederich et al. | | 2003/0098249 A1 | 5/2003 | Rollock |
| 5,468,148 A | 11/1995 | Ricks | | 2003/0213075 A1 | 11/2003 | Hui et al. |

| | | | |
|---|---|---|---|
| 2004/0122377 | A1 | 6/2004 | Fischer et al. |
| 2004/0209222 | A1 | 10/2004 | Snyder et al. |
| 2005/0004498 | A1 | 1/2005 | Klupt |
| 2005/0098565 | A1 | 5/2005 | Snyder et al. |
| 2005/0271531 | A1 | 12/2005 | Brown et al. |
| 2007/0105065 | A1 | 5/2007 | Snyder et al. |
| 2007/0202459 | A1 | 8/2007 | Boyd et al. |
| 2007/0203439 | A1 | 8/2007 | Boyd et al. |

FOREIGN PATENT DOCUMENTS

| | | |
|---|---|---|
| CH | 655237 | 4/1987 |
| DE | 1466963 | 5/1969 |
| DE | 2409752 | 9/1975 |
| DE | 2545936 | 4/1977 |
| DE | 2910982 | 2/1980 |
| EP | 0023672 | 7/1980 |
| FR | 2556954 | 6/1985 |
| FR | 2654627 | 5/1991 |
| GB | 1182031 | 2/1970 |
| GB | 2018605 | 10/1979 |
| WO | WO2004/021958 | 3/2004 |
| WO | WO2004/039205 | 5/2004 |

OTHER PUBLICATIONS

Amendment and Response to Non-Final Office Action, U.S. Appl. No. 10/749,675, 13 pages, Aug. 30, 2005.

Final Office Action, U.S. Appl. No. 10/749,675, 10 pages, Jan. 3, 2006.

Amendment and Response to Final Office Action, U.S. Appl. No. 10/749,675, 10 pages, Mar. 3, 2006.

Advisory Action, U.S. Appl. No. 10/749,675, 3 pages, Mar. 16, 2006.

Notice of Allowance, U.S. Appl. No. 10/749,675, 9 pages, Jul. 3, 2006.

The Right Tool, Electron Fusion Devices, Inc., 2 pages, at least as early as Feb. 1991.

Brochure: Woog International, "You have a 98% chance of getting gum disease. Unless you read this.", Lancaster, Pennsylvania, Feb. 1987.

Brochure: Woog International, "We put the control of home dental care back into the hands of the professional", Lancaster, Pennsylvania, Feb. 1987.

Brochure: WOOG International, "Products at a Glance: Home Dental Care System" WOOG ORAJET, at least as early as Dec. 18, 1998.

Website: http://www.just4teeth.com/product/Panasonic/Panasonic_Portable_Irrigator.htm, 2 pages, at least as early as Jun. 20, 2003.

Website: http://www.videodirectstore.com/store/merchant.mv?Screen=PROD&Product_Code=EW1'..., 2 pages, at least as early as Jun. 20, 2003.

Website: http://www.products.consumerguide.com/cp/family/review/index.dfm/id/18742, 2 pages, at least as early as Jun. 20, 2003.

Website: http://www.racekarteng.com/images/walbroparts.gif and http://www.muller.net/mullermachine/docs/walbro1.html, 4 pages, at least as early as Jun. 20, 2003.

European Search Report, EPO Application No. 07252693.2, 14 pages, Apr. 28, 2008.

Non-Final Office Action, U.S. Appl. No. 11/609,224, 33 pages, Jun. 24, 2009.

US RE27,274, 01/1972, Mattingly (withdrawn)

* cited by examiner

ORAL IRRIGATOR

FIELD OF THE INVENTION

The present invention relates to health and personal hygiene equipment and methods of controlling such equipment. More particularly, the present invention relates to oral irrigators and methods of controlling such equipment.

BACKGROUND OF THE INVENTION

Oral irrigators for discharging a high-pressure fluid stream into a user's oral cavity are well known in the art and are useful for promoting oral hygiene and health. For example, a particularly effective oral irrigator is disclosed in U.S. patent application Ser. No. 10/749,675 which is hereby incorporated by reference in its entirety into the present application.

It is advantageous for an oral irrigator to discharge a fluid stream at a select pulse rate that is generally constant. For example, a particularly useful constant pulse rate is 1200 cycles per minute.

Depending on the user and the part of the oral cavity being impacted by the fluid stream, a high-pressure fluid stream or a low-pressure fluid stream may be preferred. Thus, it is preferable to offer oral irrigators with an ability to vary the pressure of the fluid stream discharging from the oral irrigator. Prior art oral irrigators have attempted to meet this need by adjusting pumping speed. Unfortunately, this approach results in an inability of the oral irrigator to provide a generally constant pulse rate.

There is a need in the art for an oral irrigator that offers discharge pressure control while still maintaining a generally constant pulse rate. There is also a need in the art for a method of controlling the pressure of a fluid stream discharging from the oral irrigator while still maintaining a generally constant pulse rate.

SUMMARY OF THE INVENTION

The present invention, in one embodiment, is a handheld oral irrigator comprising a fluid reservoir, a pump, a pressure control assembly, and a nozzle. The pump includes a suction side and a discharge side. The suction side is in fluid communication with the fluid reservoir. The pressure control assembly includes a casing and a member displaceable within the casing. The casing has an inlet and an outlet. The inlet is in fluid communication with the discharge side of the pump, and the nozzle is in fluid communication with the outlet of the casing.

In one embodiment, the member is longitudinally displaceable within the casing. In one embodiment, the oral irrigator also includes an actuator for displacing the member within the casing and wherein the member comprises a portion that extends through the casing to couple to the actuator. In one embodiment, the portion of the member is an arm that extends through a longitudinally extending slot in the casing. In one embodiment, a fluid flow path extending from the inlet to the outlet is modifiable between a first route that extends along at least a portion of the member and a second route that does not.

The present invention, in one embodiment, is an oral irrigator comprising a pump, a discharge nozzle and a pressure control. The pump has a generally constant operating speed and feeds the discharge nozzle. The pressure control is adapted to modify a discharge pressure at the nozzle without a significant change in pump speed. The pressure control modifies a level of fluid flow restriction between the pump and the nozzle. In one embodiment, the pressure control modifies the diameter of a fluid flow path extending through the pressure control. In one embodiment, the pressure control modifies the length of a fluid flow path extending through the pressure control. In one embodiment, the pressure control modifies the number of direction changes of a fluid flow path extending through the pressure control.

The present invention, in one embodiment, is an oral irrigator comprising a pump and a pressure adjustment assembly. The pump supplies a nozzle. The pressure adjustment assembly is configured to provide a first fluid flow path associated with a high nozzle discharge pressure and a second fluid flow path associated with a low nozzle discharge pressure. The pressure adjustment assembly is located between the pump and nozzle.

In one embodiment, the first fluid flow path offers a more direct route to the nozzle than the second fluid flow path. In one embodiment, the first fluid flow path has a length that is shorter than a length of the second fluid flow path. In one embodiment, the second fluid flow path has a diameter that is smaller than a diameter of the first fluid flow path.

In one embodiment, the pressure adjustment assembly includes a casing and a member displaceable within the casing. The casing includes an orifice and the member includes an orifice. The second fluid flow path extends through both orifices. The first fluid flow path extends only through the orifice of the casing.

In one embodiment, the pressure adjustment assembly includes a casing and a member displaceable within the casing. A portion of the second fluid flow path extends circumferentially about at least a portion of the member. In one embodiment, the member is generally cylindrical and includes a groove extending about at least a portion of the circumferential outer surface of the member. The casing includes an inlet orifice that aligns with the groove to form a portion of the second fluid flow path. The member includes a longitudinally extending center lumen in fluid contact with the groove via an orifice extending through a wall of the member.

The present invention, in one embodiment, is an oral irrigator comprising a pump and a pressure adjustment assembly. The pump supplies a nozzle. The pressure adjustment assembly comprises a first fluid flow friction setting associated with a high nozzle discharge pressure and a second fluid flow friction setting associated with a low nozzle discharge pressure.

The present invention, in one embodiment, is a method of controlling a nozzle discharge pressure of an oral irrigator that includes a pump that feeds a nozzle. The method comprises modifying a fluid flow friction value of a fluid flow path between the pump and nozzle by modifying the fluid flow path. In one embodiment, the fluid flow path is modified by changing its length. In one embodiment, the fluid flow path is modified by changing its diameter. In one embodiment, the fluid flow path is modified by changing its number of direction deviations.

The present invention, in one embodiment, is an oral irrigator including a handle portion and a faceplate. The faceplate is selectively attachable to the handle portion to customize an appearance of the oral irrigator.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION OF THE INVENTION

The subject invention, in one embodiment, is a handheld oral irrigator 10 that allows a user to adjust the discharge pressure of the irrigator generated fluid stream while maintaining the pulse rate of the fluid stream. Thus, the handheld oral irrigator 10 is advantageous over the prior art because it allows a user to adjust the fluid stream discharge pressure to suit the user's comfort preference, while still allowing the oral irrigator to supply the fluid stream at a preferred or most effective pulse rate (e.g., 1200 cycles per minute).

Figure 1:
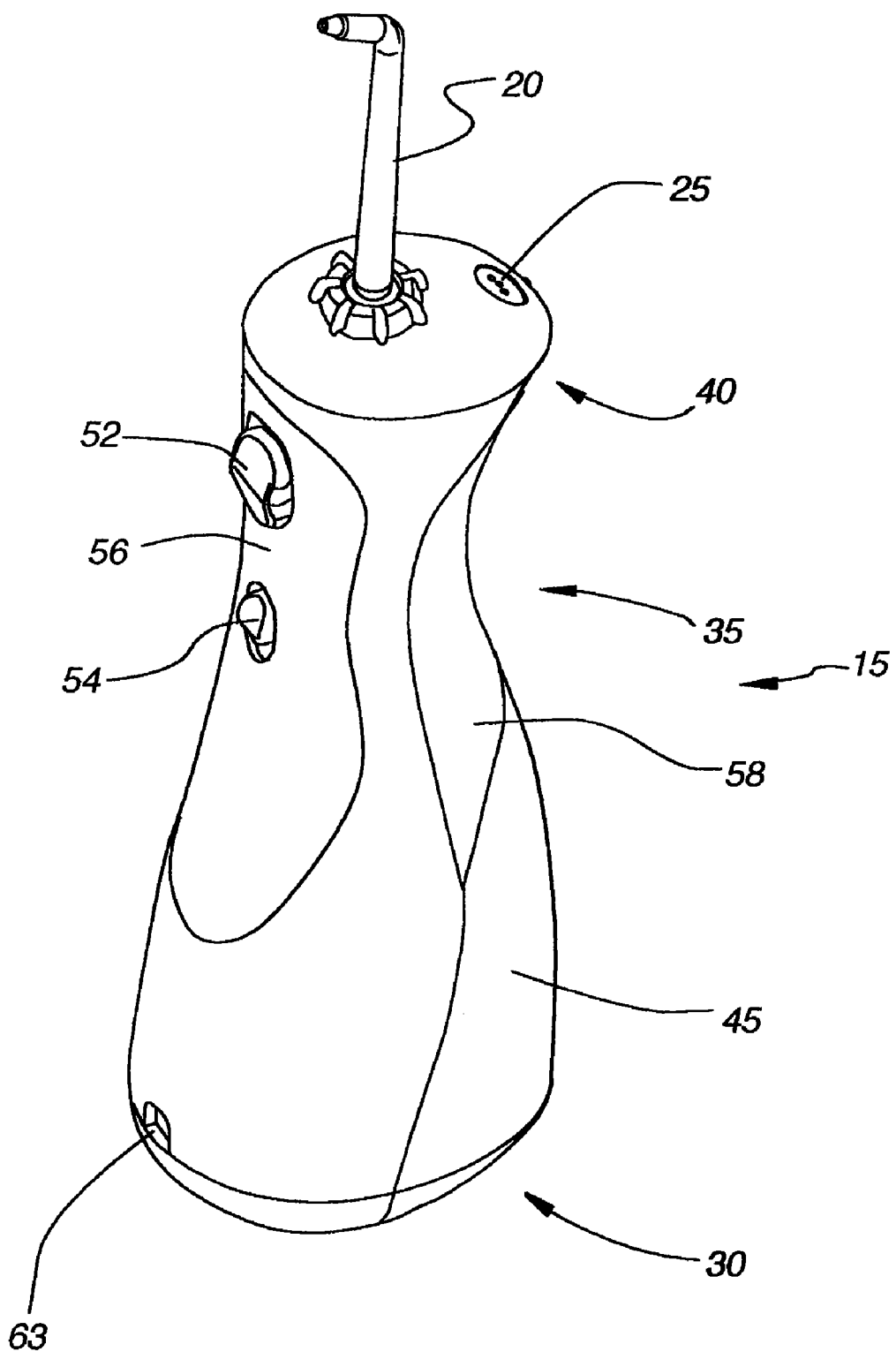
FIG. 1 is a top isometric view of the handheld oral irrigator.
Figure 2:
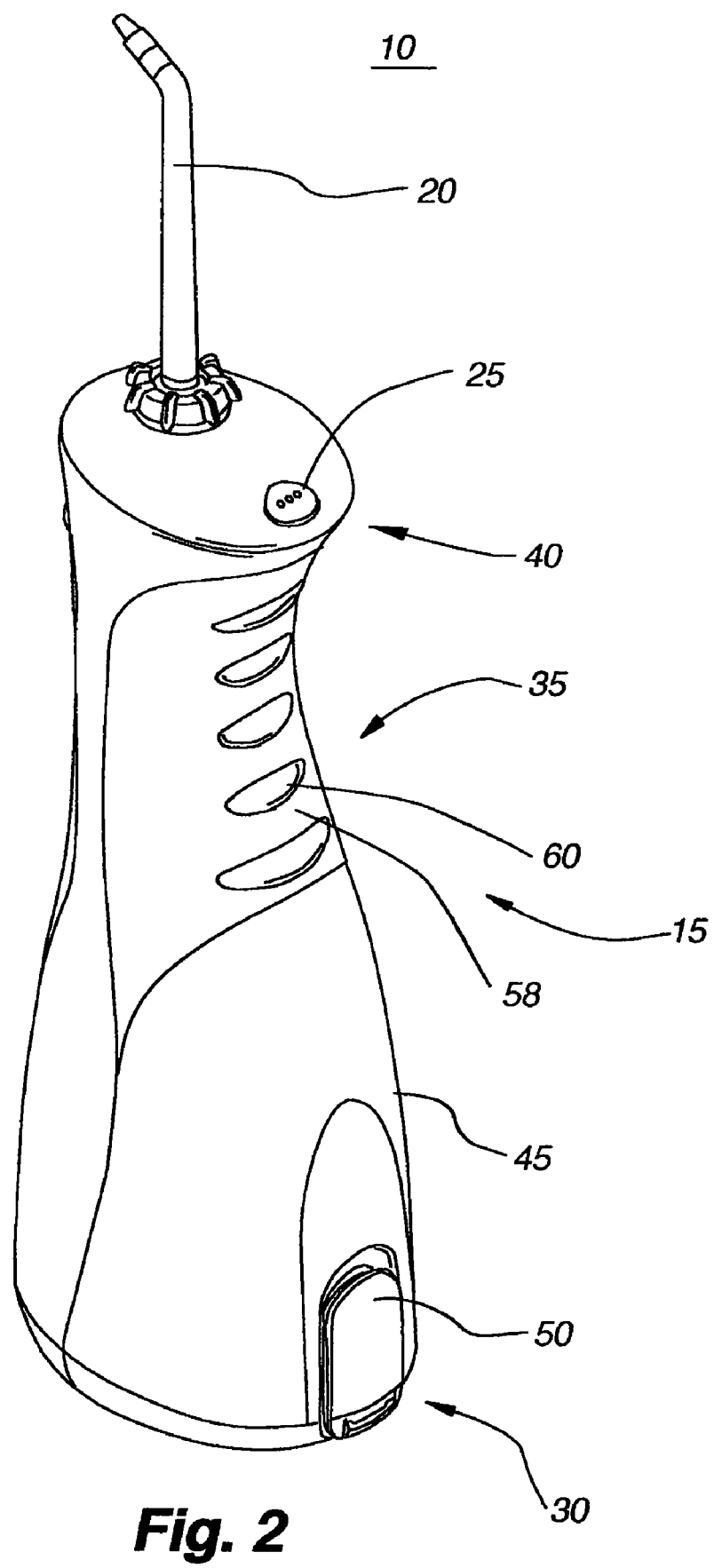
FIG. 2 is a top isometric view of the handheld oral irrigator.
Figure 3:
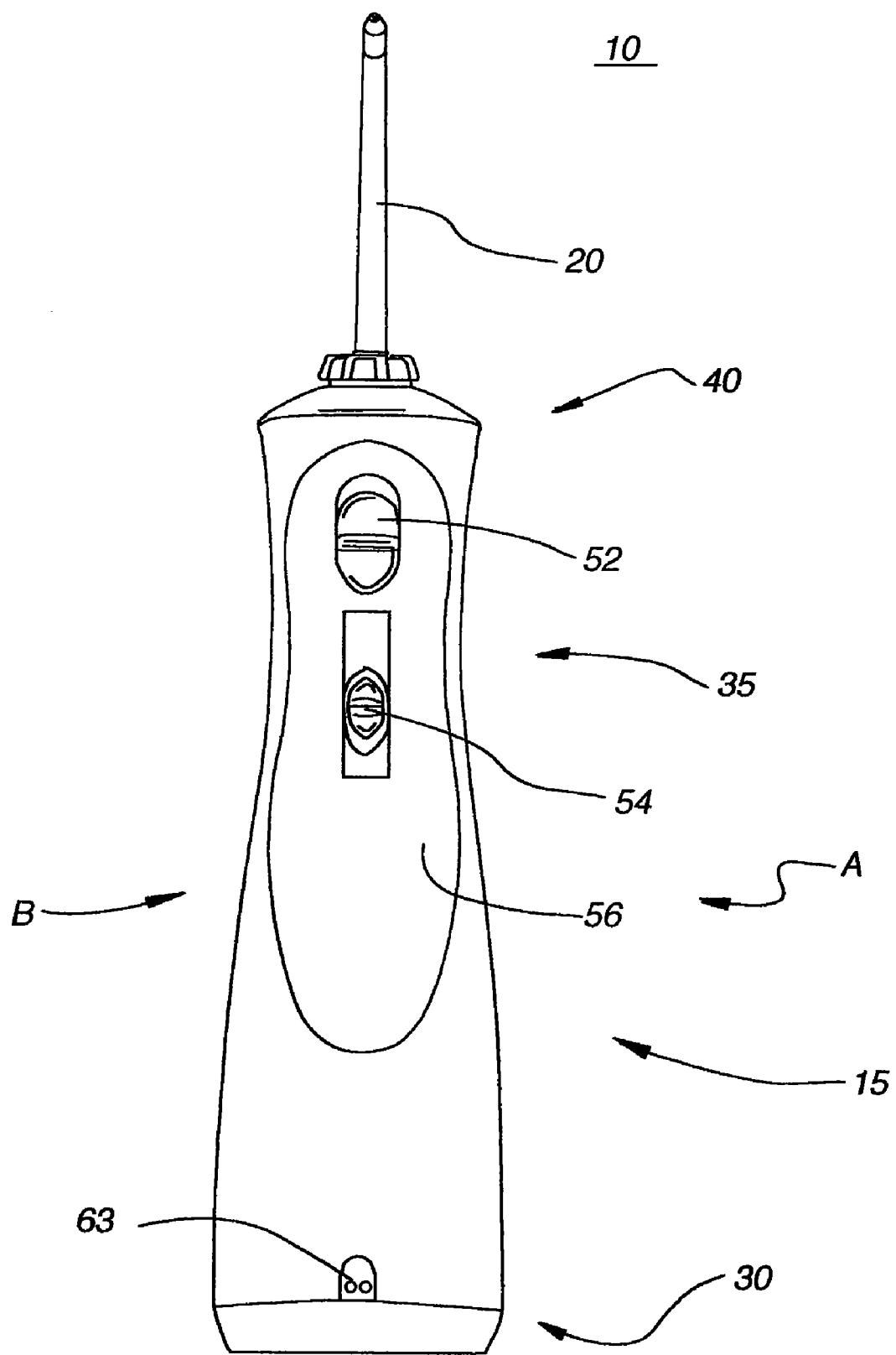
FIG. 3 is a control side elevation of the handheld oral irrigator.
Figure 4:
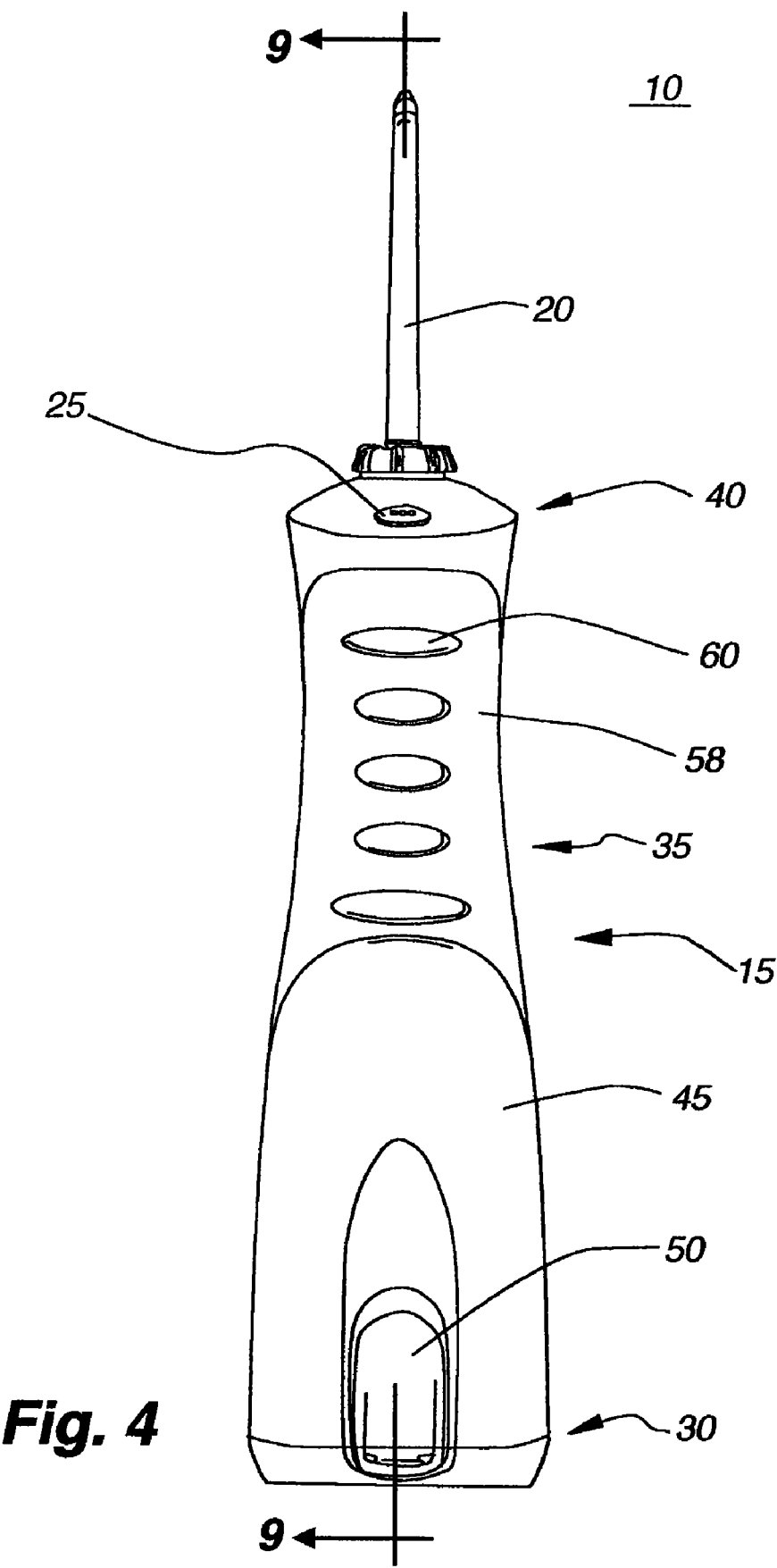
FIG. 4 is a reservoir side elevation of the handheld oral irrigator.
Figure 5:
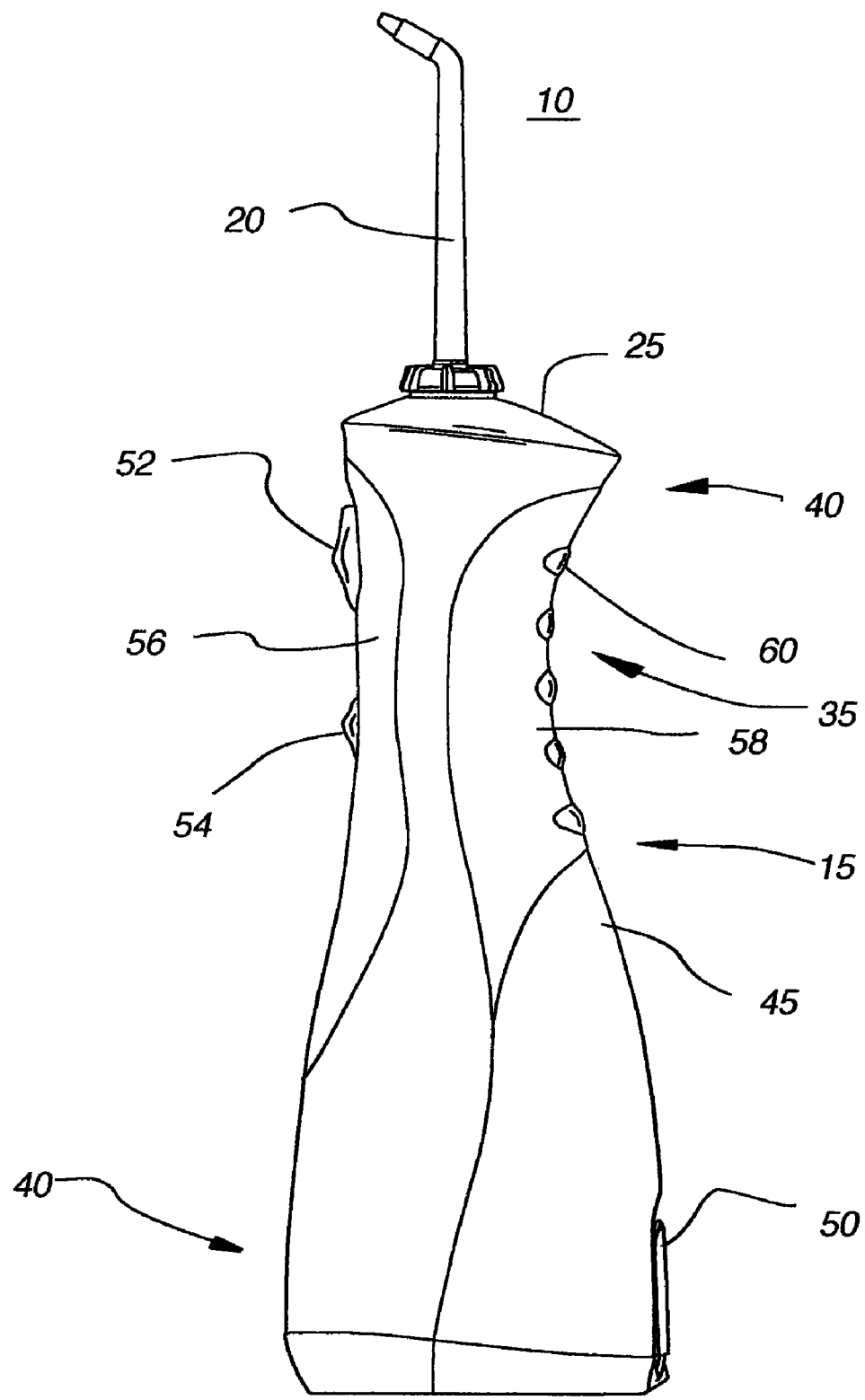
FIG. 5 is a right side elevation of the handheld oral irrigator as if viewed from the direction of arrow A in FIG. 3.
Figure 6:
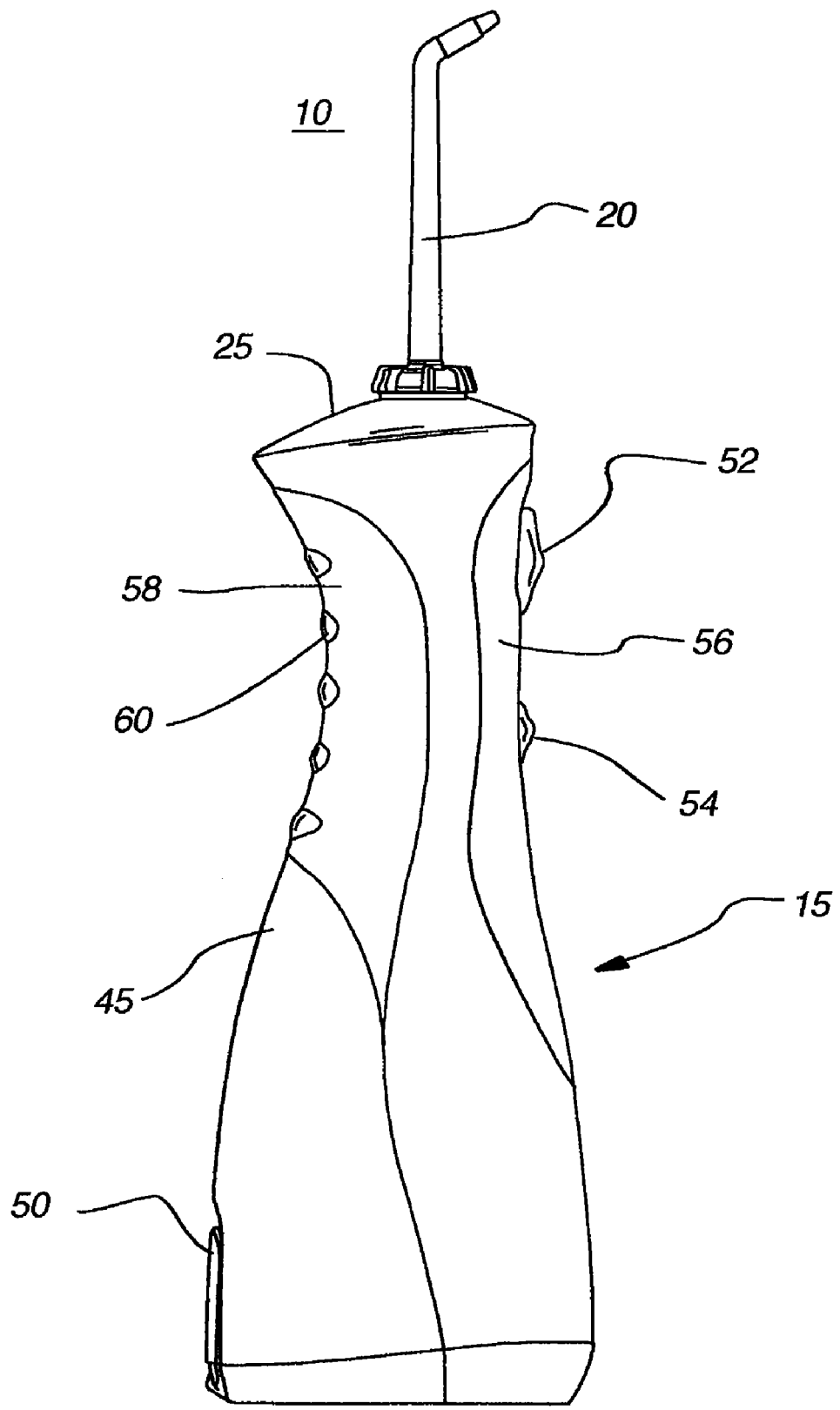
FIG. 6 is a left side elevation of the handheld oral irrigator as if viewed from the direction of arrow B in FIG. 3.
Figure 7:
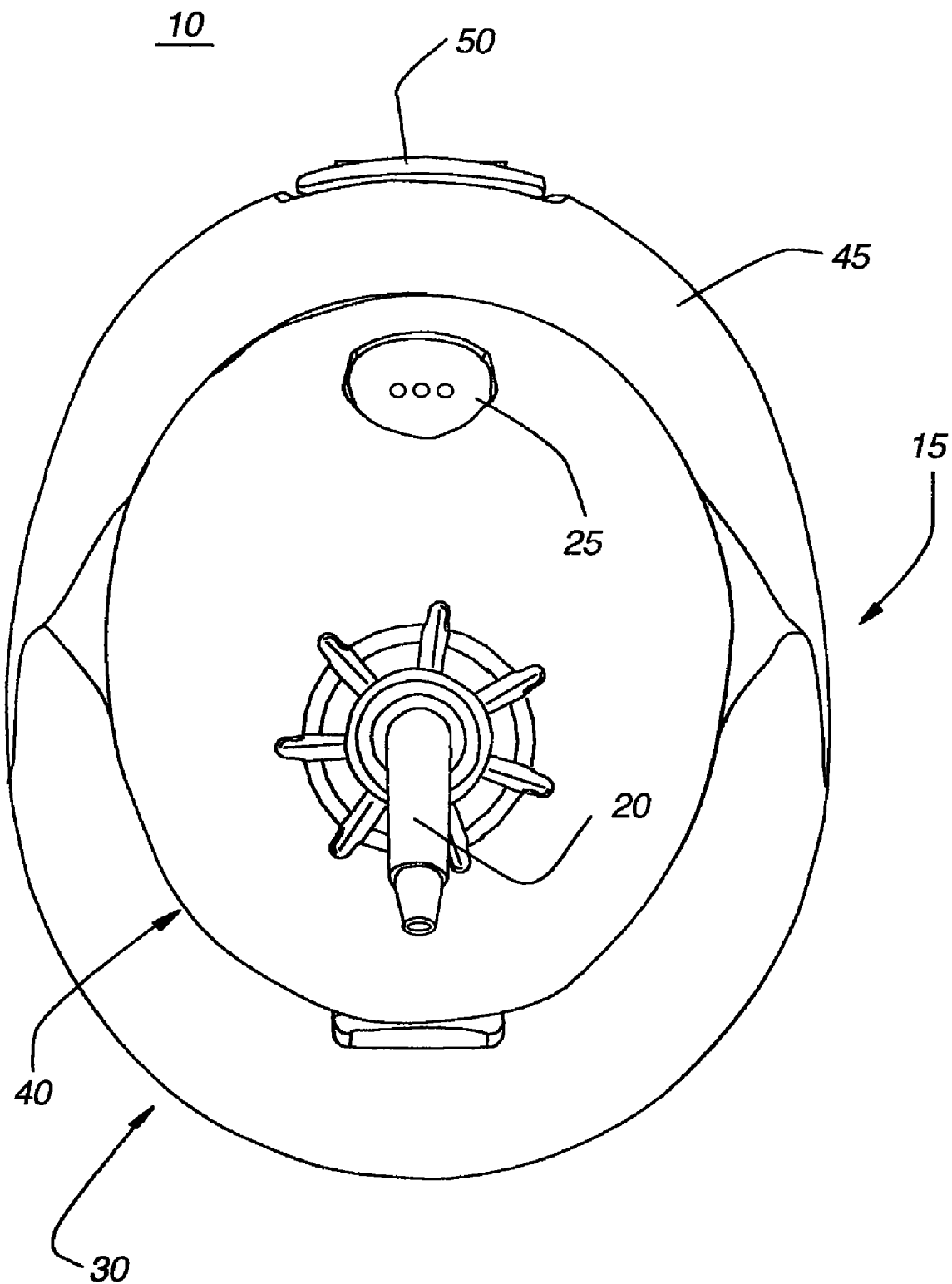
FIG. 7 is a top plan view of the handheld oral irrigator.
Figure 8:
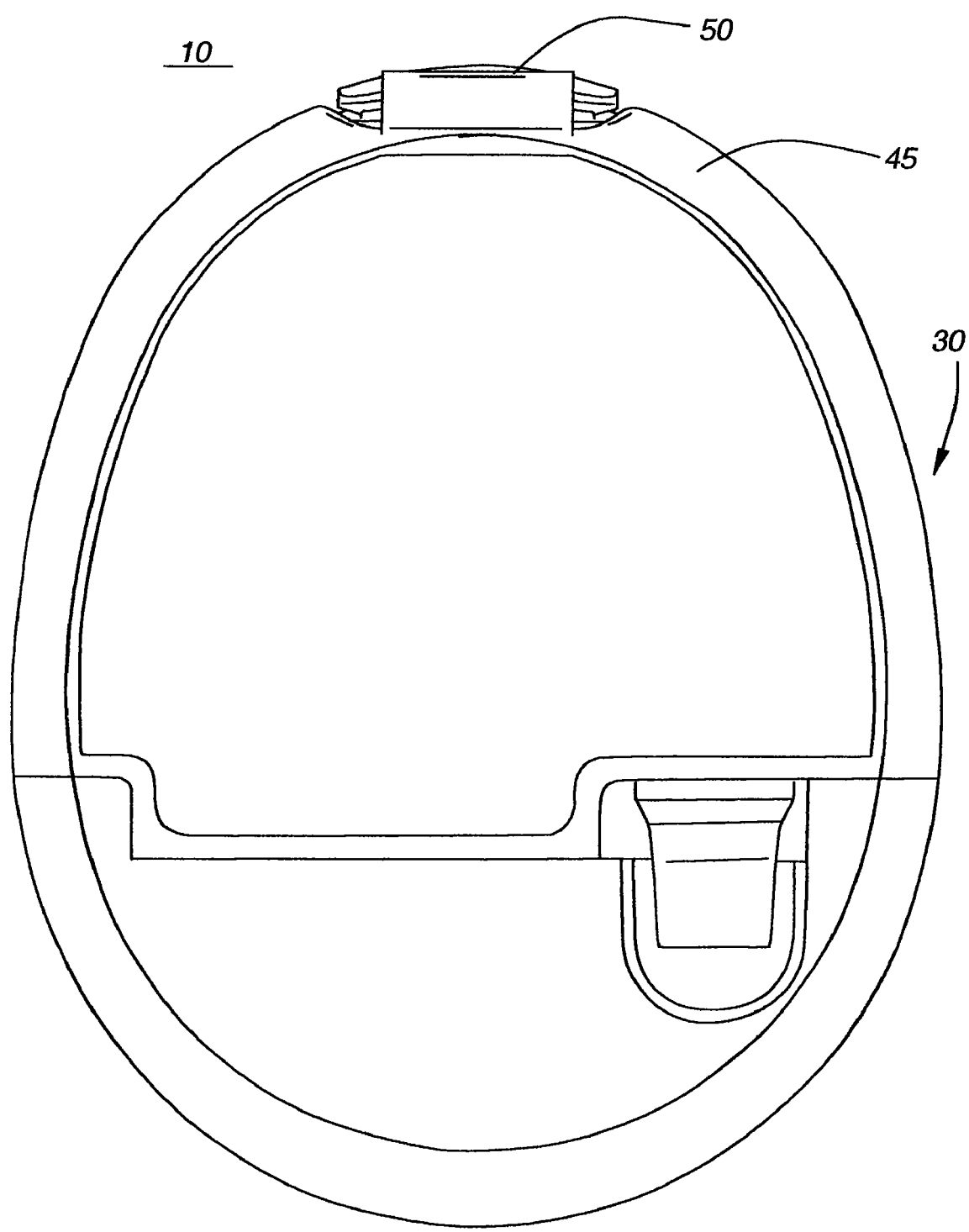
FIG. 8 is a bottom plan view of the handheld oral irrigator.

For a discussion of the overall external configuration of one embodiment of the handheld oral irrigator 10, reference is made to FIGS. 1-8. FIGS. 1 and 2 are top isometric views of the handheld oral irrigator 10. FIG. 3 is a control side elevation of the handheld oral irrigator 10. FIG. 4 is a reservoir side elevation of the handheld oral irrigator 10. FIG. 5 is a right side elevation of the handheld oral irrigator 10 as if viewed from the direction of arrow A in FIG. 3. FIG. 6 is a left side elevation of the handheld oral irrigator 10 as if viewed from the direction of arrow B in FIG. 3. FIG. 7 is a top plan view of the handheld oral irrigator 10. FIG. 8 is a bottom plan view of the handheld oral irrigator 10.

As shown in FIGS. 1-7, in one embodiment, the irrigator 10 includes a handle portion 15 and a nozzle 20 with an orthodontic tip at its distal end. The nozzle 20 extends from a top end of the handle portion 15. The nozzle 20 is detachable from the handle portion 15 via a nozzle release button 25 located on the top of the handle portion 15.

As illustrated in FIGS. 1-6, in one embodiment, the handle portion 15 has a modified hourglass shape that gradually narrows from a wide base 30 (the proximal end of the irrigator 10) to a narrow gripping area 35 and gradually widens from the narrow gripping area 35 to a moderately wide top 40 (the distal end of the irrigator 10). The hourglass shape is aesthetically pleasing and ergonomically shaped to accommodate a user's hand, which in one embodiment will be a child or adolescent hand.

As indicated in FIGS. 1, 2 and 4-8, in one embodiment, the handle portion 15 includes a reservoir 45 that forms a part of the base 30. The reservoir 45 is removable from the rest of the handle portion 15 and includes a fill port 50 near the bottom of the reservoir 45. To fill the reservoir with fluid, the reservoir 45 may be disengaged and removed from the rest of the handle portion 15, the cap of the fill port 50 is opened, and a fluid is flowed into the reservoir 45 via the open fill port 50. Once the reservoir 45 is filled, the cap is closed on the fill port 50 and the reservoir 45 is reattached to the rest of the handle portion 15.

As can be understood from FIGS. 1, 2 and 4-8, the reservoir 45 may be filled while still attached to the rest of the handle portion 15. To do this, the cap of the fill port 50 is opened and a fluid is flowed into the reservoir 45 via the open fill port 50. Once the reservoir 45 is filled, the cap is closed.

Figure 25:
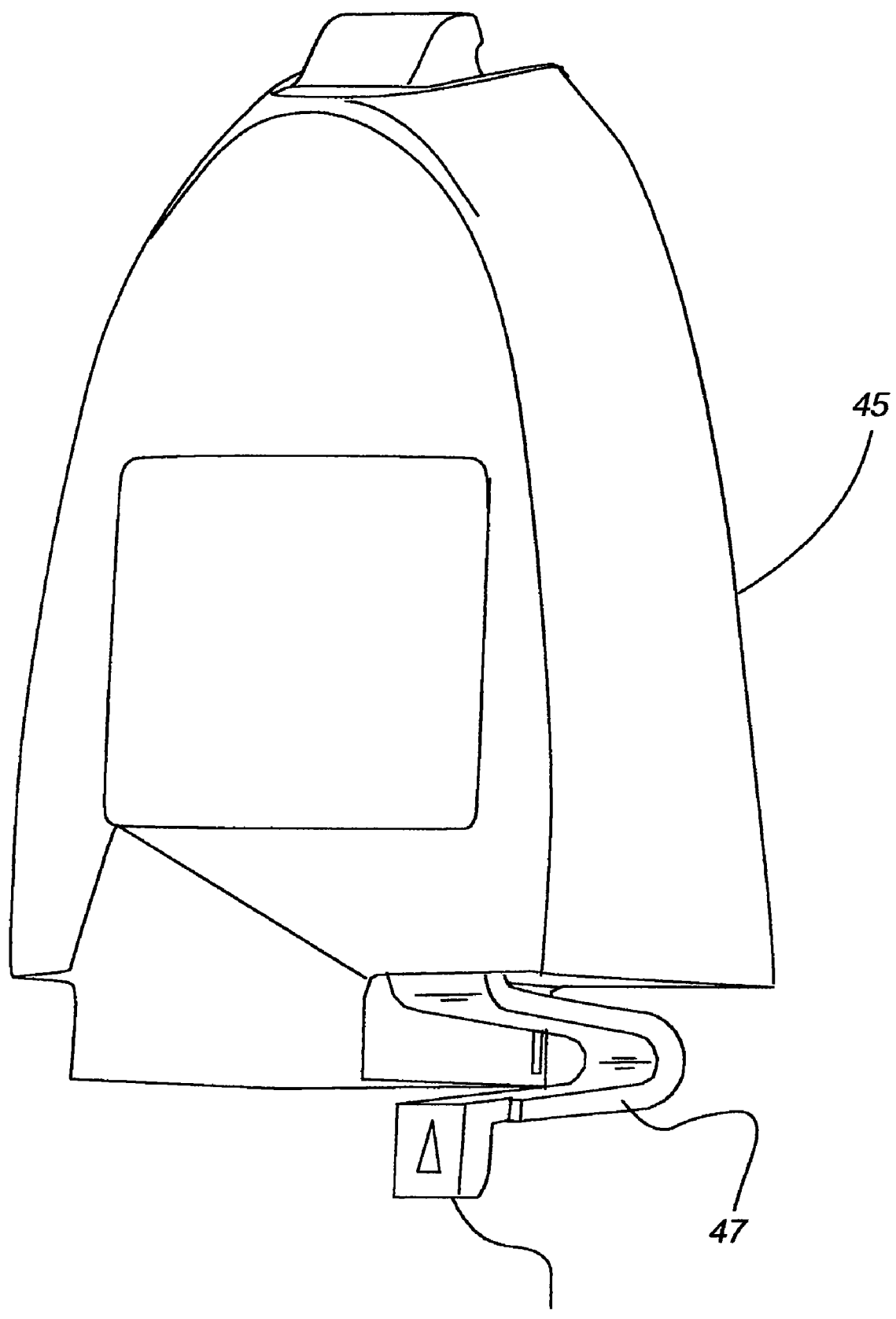
FIG. 25 is a bottom perspective view of a reservoir of the handheld oral irrigator.

For a discussion regarding disengaging the reservoir 45 from the rest of the handle portion, reference is made to FIGS. 8 and 25, wherein FIG. 25 is a bottom perspective view of the reservoir of the handheld oral irrigator. As best shown in FIGS. 8 and 25, the reservoir 45 includes a leaf spring latch 47 molded into a lower portion of the reservoir 45 to releasably secure the reservoir 45 to the handle portion 15. The leaf spring latch 47 is biased to engage the handle portion 15 when the reservoir 45 is joined with the handle portion 15. To disengage the leaf spring latch 47 from the handle portion 15, the user moves a latch portion 49 of the leaf spring latch 47 in the direction indicated by an arrow formed, printed, or placed on the leaf spring latch 47. In one embodiment, the reservoir 45 moves downwardly relative to the handle portion 15 when the leaf spring latch 47 is disengaged from the handle portion 15.

Referring again to FIGS. 1, 3 and 5-7 for a continued discussion of the overall external configuration of the handheld oral irrigator, in one embodiment, a control side of the gripping area 35 includes an on/off control 52, a pressure control 54, and a removable faceplate 56 that surrounds the locations of the two controls 52, 54. The on/off control 52 allows a user to turn on or shut off the irrigator 10. To turn the irrigator 10 on, the on/off control 52, which can be a slide, button, etc., is moved (e.g., slid or depressed) to complete an electrical circuit between the irrigator's internal power source and its motor. To turn the irrigator 10 off, the control 52 is moved again to break the electrical circuit.

The pressure control 54 allows a user to adjust the discharge pressure of a fluid stream discharging from the distal tip of the nozzle 20. In one embodiment, the nozzle release button 25 is located on the reservoir side opposite from the controls 50, 52, which helps limit accidental release of the nozzle 20 by accidental pressing or other engagement of the nozzle release button 25 when the user operates the controls 50, 52.

The removable faceplate 56 can be replaced with other faceplates having other colors or designs, thereby allowing the user to customize the appearance of the irrigator 10 as preferred. In one embodiment, the handheld oral irrigator 10 is sold or provided with multiple faceplates 56 of various designs and colors. The user selects their preferred faceplate and mounts it on the handle portion 15.

Figure 26:
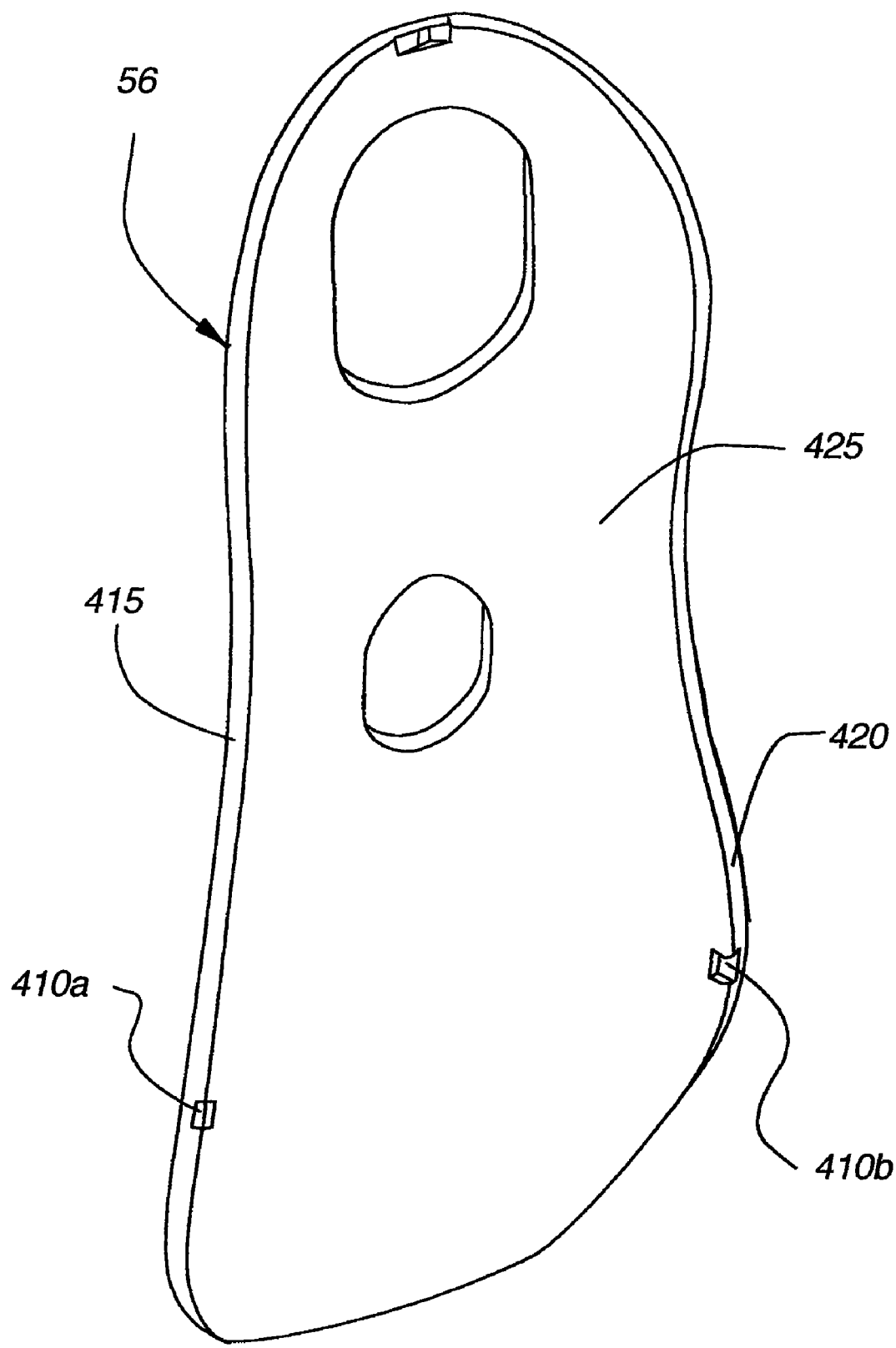
FIG. 26 is a rear perspective view of a removable faceplate of the handheld oral irrigator.

As shown in FIG. 26, which is a rear perspective view of the removable faceplate of the handheld oral irrigator, the removable face plate 56 has two or more L-shaped tabs 410a, 410b for receipt in corresponding slots or grooves defined in the handle portion 15 of the oral irrigator 10 to join the removable faceplate 56 to the handle portion 15. When joined together, the short legs of the tabs 410a, 410b are received in the slots or grooves defined in the handle portion 15 to maintain the joined relationship between the removable faceplate 56 and the handle portion 15.

To disconnect the removable faceplate 56 from the handle portion 15, the removable faceplate 56 is sufficiently flexible such that a user can deflect the edges 415,420 of the removable faceplate 56 inward in order disengage the tabs 410a, 410b from the handle portion 15 to pull the faceplate 56 away from the handle portion 15. As a user moves the edges 415, 420 of the removable faceplate 56 inwardly, the short legs of the tabs 410a, 410b are removed from the slots or grooves in the handle portion 15, thereby allowing the user to remove the removable faceplate 56 from the handle portion 15.

To join the removable faceplate 56 to the handle portion 15, a user deflects the edges 415, 420 of the removable faceplate 56 inwardly and abuts a rear facing surface 425 of the removable faceplate 56 against the handle portion 15. When the removable faceplate 56 abuts the handle portion 15 in the proper location and orientation, the short legs of the tabs 410a,410b generally align with the grooves or slots in the handle portion 15. In one embodiment, the handle portion 15 has a recessed surface surrounding the controls 50, 52 to aid a user in properly locating and orienting the removable faceplate 56 relative to the handle portion. 15. Once the removable faceplate 45 abuts the handle portion 56 in the proper location and orientation, the user stops squeezing the edges 415, 420 of the removable faceplate inwardly, thereby causing the short legs of the tabs 410a, 410b, which are biased to move outwardly by the internal forces generated by inward movement of the edges 415, 420 of the removable faceplate 56, to enter into the grooves or slots defined in the handle portion 15.

Referring again to FIGS. 1, 3 and 5-7 for a continued discussion of the overall external configuration of the handheld oral irrigator, the reservoir side of the gripping area 35 includes a soft over molded grip area 58, which in one embodiment, includes gripping bumps 60, a textured gripping surface, or other grip enhancing features.

As illustrated in FIGS. 1 and 3, in one embodiment, a charging plug 63 exits in the handle portion 15 near the base 30. The charging plug 63 is used to place an external power source in electrical communication with an internal power source (e.g., battery) located within the handle portion 15.

Figure 9:
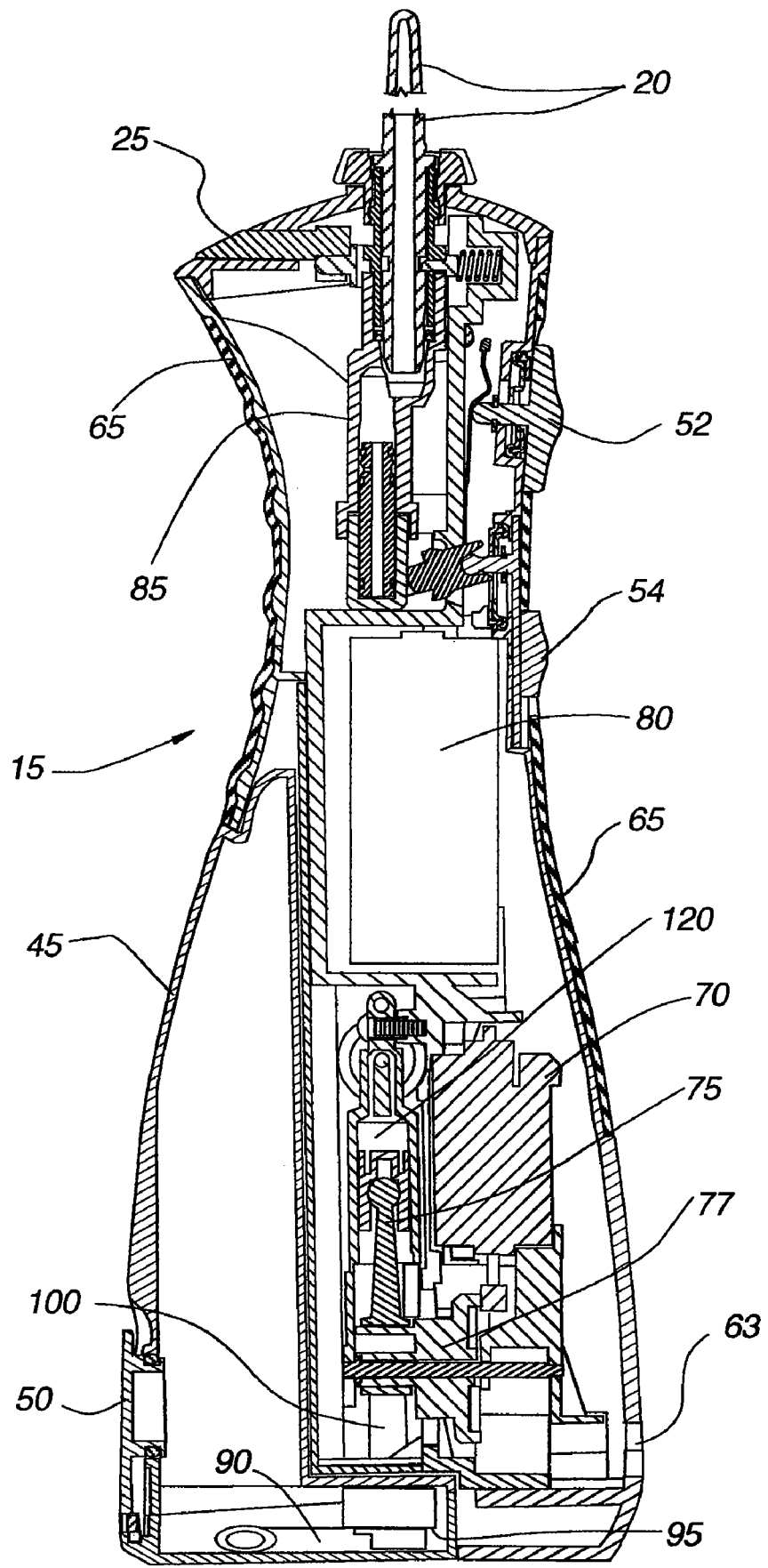
FIG. 9 is a section elevation of the handheld oral irrigator as taken along section line 9-9 in FIG. 4.
Figure 10:
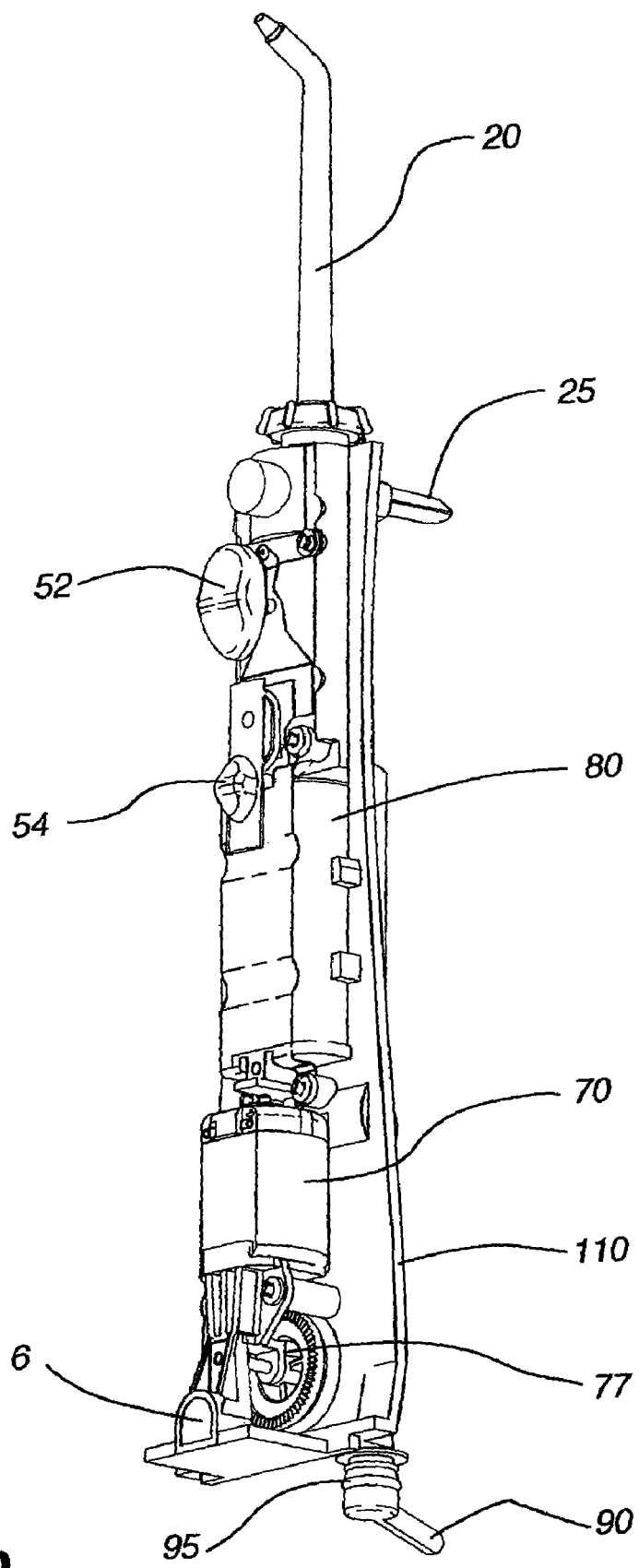
FIG. 10 is an isometric view of a motor side of the handheld oral irrigator with the outer housing of the handle portion removed to show the internal elements of the irrigator.
Figure 11:
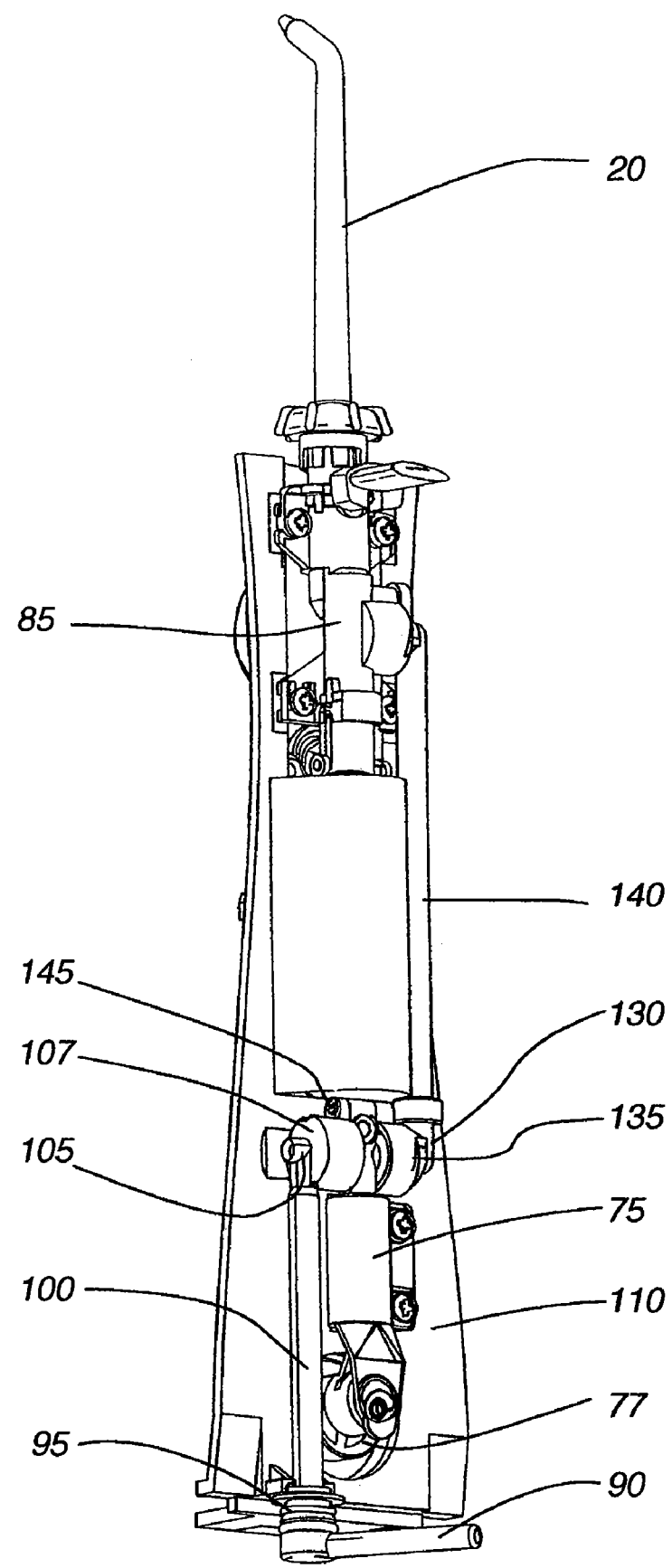
FIG. 11 is the same type of view as illustrated in FIG. 10, except of a pump side of the handheld oral irrigator.
Figure 23:
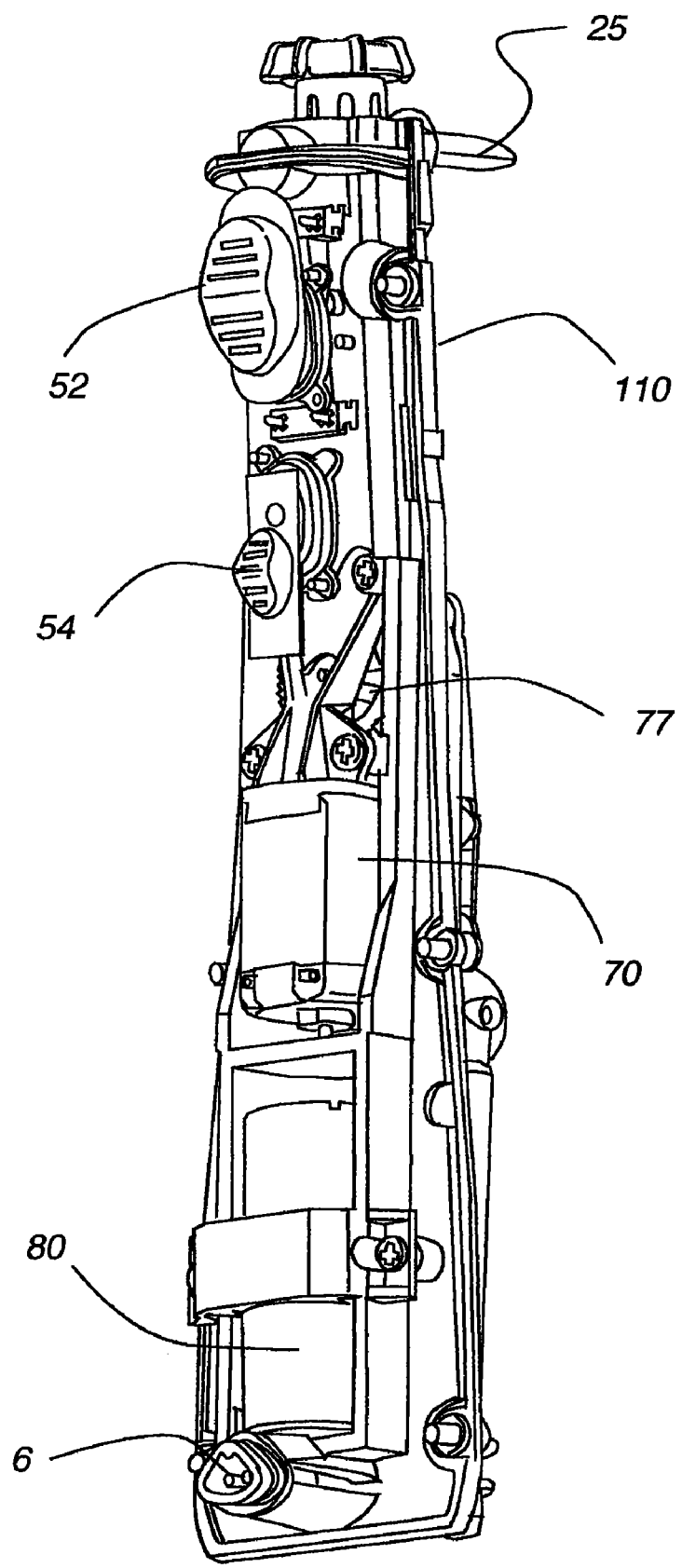
FIG. 23 is a similar view as illustrated in FIG. 10, except various components are shown in an alternate configuration.
Figure 24:
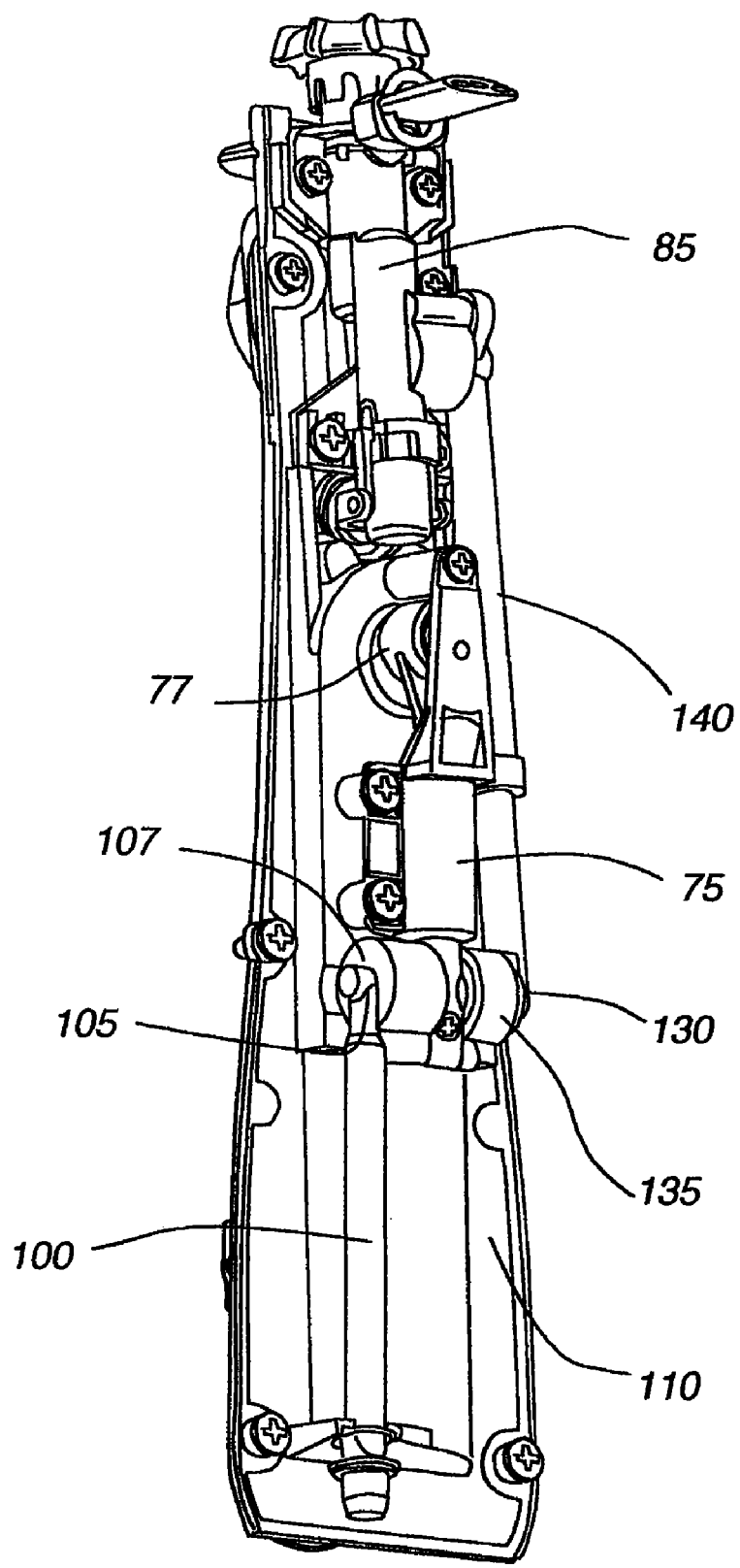
FIG. 24 is a similar view as illustrated in FIG. 11, except various components are shown in an alternate configuration.

For a discussion of the overall internal configuration of one embodiment of the handheld oral irrigator 10, reference is made to FIGS. 9-11, 23 and 24. FIG. 9 is a section elevation of the handheld oral irrigator 10 as taken along section line 9-9 in FIG. 4. FIG. 10 is an isometric view of a motor side of the handheld oral irrigator 10 with the outer housing 65 of the handle portion 15 removed to show the internal elements of the irrigator 10. FIG. 11 is the same type of view as illustrated in FIG. 10, except of a pump side of the handheld oral irrigator 10. FIG. 23 is a similar view as illustrated in FIG. 10, except various components are shown in an alternate configuration. FIG. 24 is a similar view as illustrated in FIG. 11, except various components are shown in an alternate configuration.

As shown in FIG. 9, the irrigator 10 includes an outer housing 65 that forms the exterior surface of the handle portion 15. The housing 65 encloses a motor 70, a pump 75, a transmission 77, a rechargeable NiCad battery 80, and a pressure control valve assembly 85. In one embodiment as illustrated in FIGS. 10 and 11, the motor 70 and pump 75 are located in a side-by-side arrangement near the base 30, the transmission 77 is located below the motor 70 and pump 75, the battery 80 is located above the motor 70 and pump 75, and the valve assembly 85 is located above the battery 80. In another embodiment as illustrated in FIGS. 23 and 24, the battery 80 is located near the base 30, the motor 70 and pump 75 are located above the battery 80, the transmission 77 is located above the motor 70 and pump 75, and the valve assembly 85 is located above the transmission 77. The transmission 77 couples the motor 70 to the pump 75 to convert the rotational output of the motor 70 into the longitudinally reciprocating movement of the pump's piston 120.

As illustrated in FIG. 9, the removable reservoir 45 forms a significant part of a lower side of the handle portion 15. The fill port 50 opens into the reservoir 45, and the reservoir 45 extends under a portion of the housing 65 enclosing the motor 70 and pump 75. A transfer tube 90 extends from a bottom level of the reservoir 45 to a seal coupling 95. In one embodiment, the transfer tube 90 is part of the reservoir. In another embodiment, the transfer tube 90 is separate from the reservoir 45. When the reservoir 45 is coupled to the rest of the handle portion 15, the seal coupling 95 sealing mates with a bottom end of a suction tube 100, which leads to a suction port 105 of the pump 75, as best understood from FIGS. 11 and 24. Thus, the reservoir 45 is placed in fluid communication with the suction side of the pump 75.

As indicated in FIGS. 10 and 11, and FIGS. 23 and 24, the motor 70, pump 75, transmission 77 and valve assembly 85 are coupled to a chassis plate 110 longitudinally extending through the housing 65 of the handle portion 15. In one embodiment, the controls 52, 54, motor 70 and the battery 80 are located on one side of the plate 110, and the pump 70 and valve assembly 85 are located on the other side of the plate 110.

As can be understood from FIGS. 9 and 11, the suction tube 100 is detachably sealably coupled to the seal coupling 95 by coupling the reservoir 45 to the rest of the housing 65 of the handle portion 15 such that the free end of the suction tube 100 is received in the seal coupling 95. As shown in FIG. 11, fluid traveling form the reservoir 45 to the distal end of the nozzle 20 is drawn through the transfer tube 90, into the suction tube 100 at the seal coupling 95 and to the suction port 105 of the pump 75.

Figure 12:
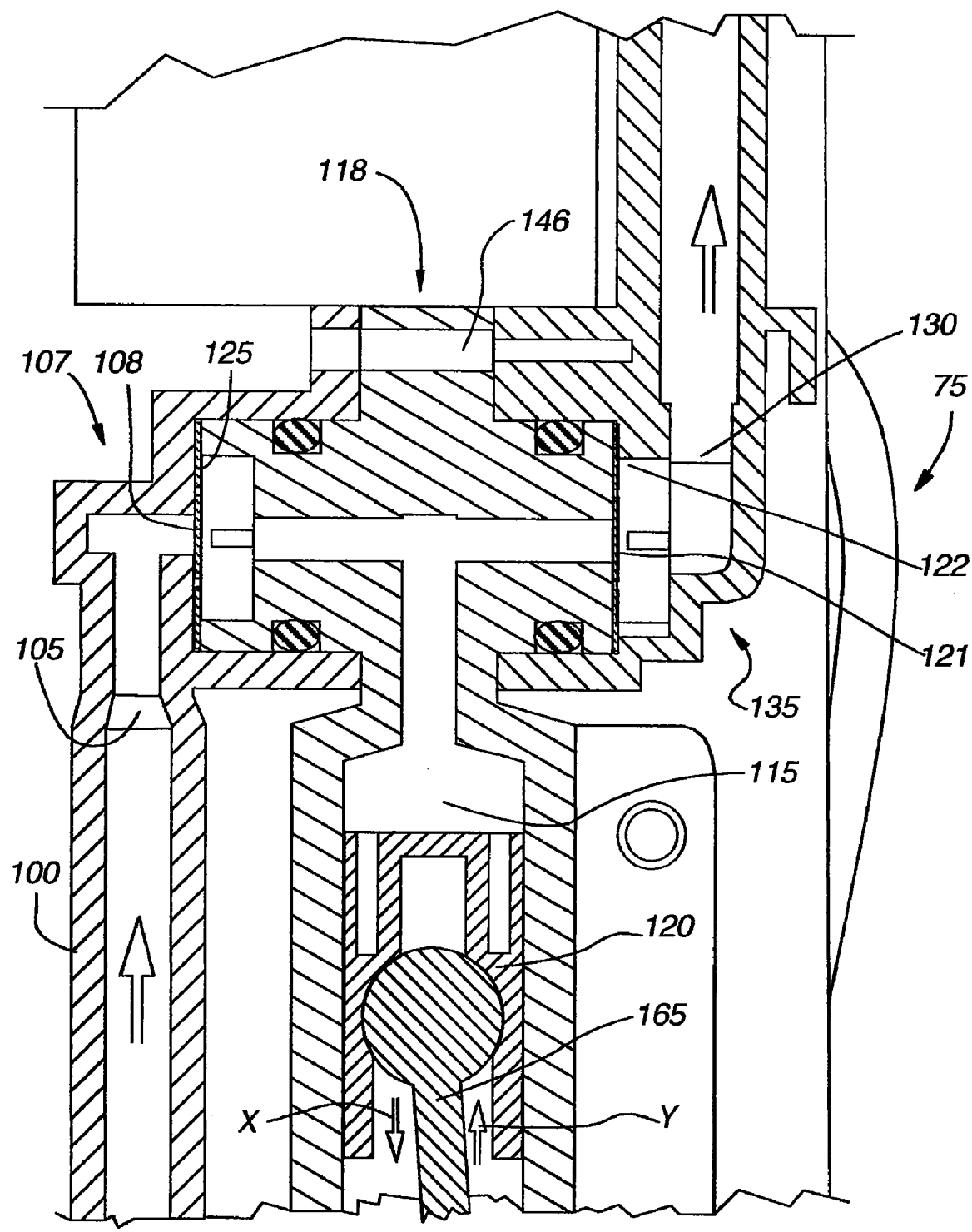
FIG. 12 is a longitudinal section through the pump.

As can be understood from FIG. 12, which is a longitudinal section through the pump 75, when a piston 120 moves rearwardly in a cylinder 115 of a cylinder casing 118 (rearward movement indicated by arrow X in FIG. 12), a discharge wafer 121 of a discharge wafer valve arrangement is forced against a discharge valve seat 122 and the fluid is drawn through the suction port 105 of a suction casing 107 of the pump 75, past a suction wafer 108 forming a suction wafer valve arrangement, and into the cylinder 115. When the piston 120 moves forwardly (as indicated by arrow Y in FIG. 12), the suction wafer 108 is forced against the suction valve seat 125 and the fluid is forced past the discharge wafer 121, into a discharge port 130 of a discharge casing 135 of the pump 75, and into a discharge tube 140 leading to the valve assembly 85, as illustrated in FIGS. 11 and 24.

In one embodiment, as depicted in FIGS. 11 and 12, the pump 75 is formed from three casings (e.g., the suction casing 107, cylinder casing 118 and discharge casing 135). In one embodiment, the three casings 107, 118, 135 are held together via a joining mechanism. For example, in one embodiment, a screw 145 (illustrated in FIG. 11) is received in screw receiving holes 146 (shown in FIG. 12) in the three casings 107, 118, 135.

Figure 13:
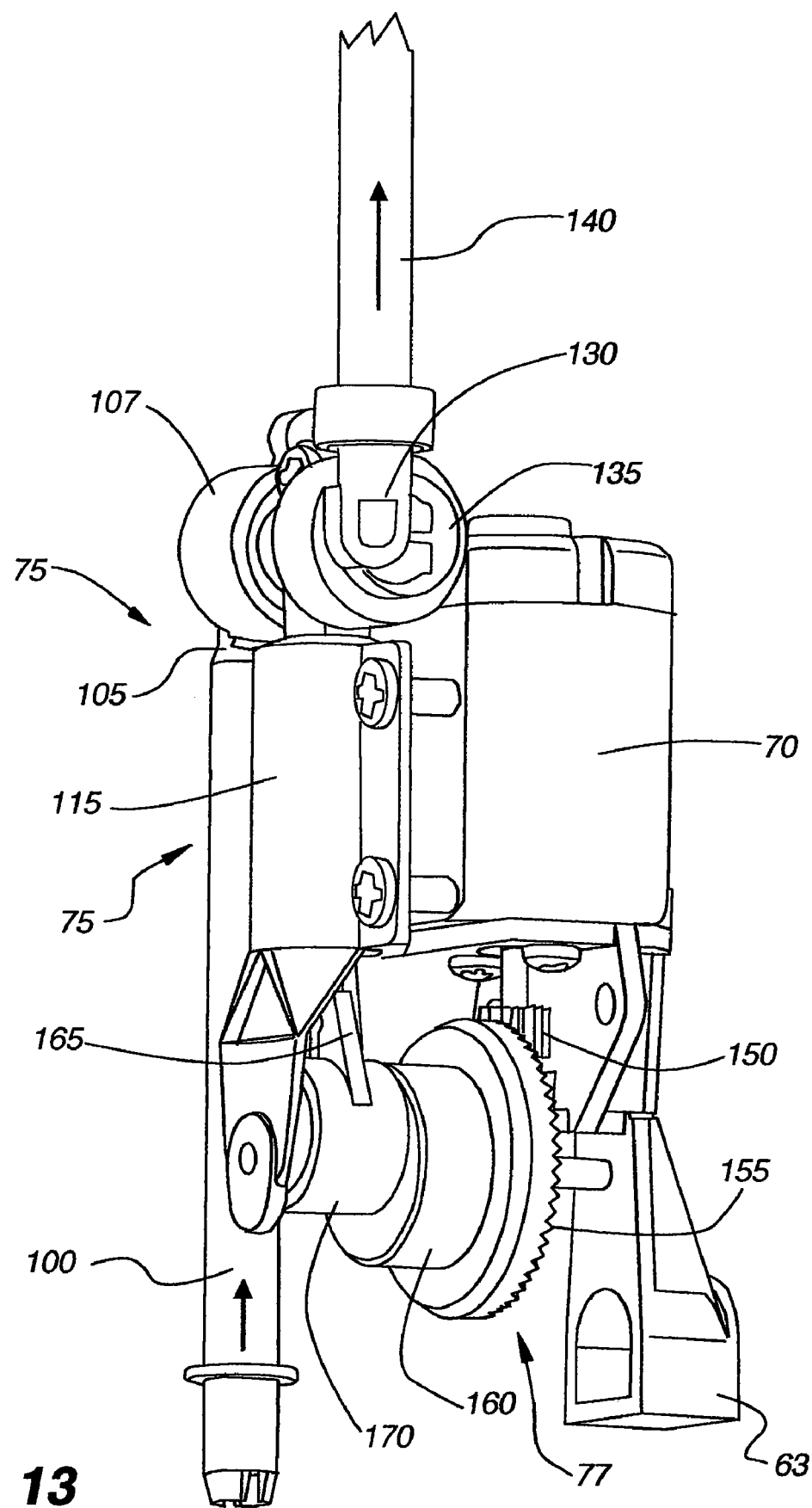
FIG. 13 is an isometric of view of the motor/pump/transmission arrangement with the rest of the irrigator 10 hidden for clarity purposes.

For a discussion of the motor/pump/transmission arrangement, reference is made to FIG. 13, which is an isometric of view of the motor/pump/transmission arrangement with the rest of the irrigator 10 hidden for clarity purposes. As shown in FIG. 12, a pinion gear 150 extends from the motor 70 to drive a gear 155 carrying a cam 160. A piston rod 165 (see FIGS. 12 and 13) extends between the piston 120 and a cam follower end 170 of the piston rod 165. The cam follower end 170 receives the cam 160, and as the cam 160 is caused to rotate, the cam follower 170 and cam 160 act to convert the rotational movement of the motor 70 into longitudinal reciprocal displacement of the piston 120 within the cylinder 115.

Figure 14:
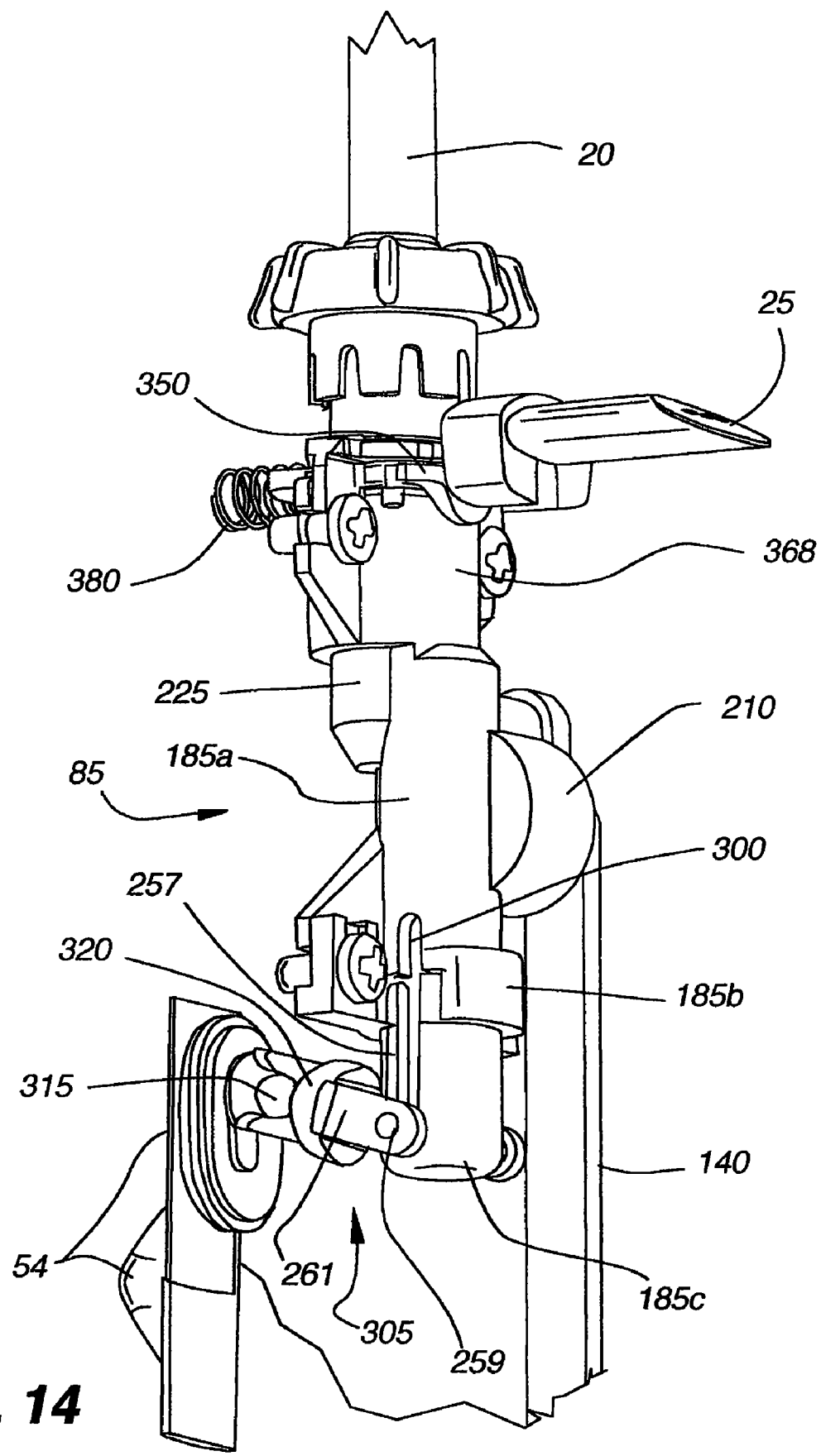
FIG. 14 is an isometric view of the pressure control valve assembly 85 with the majority of the rest of the handheld oral irrigator 10 hidden for clarity purposes.
Figure 15:
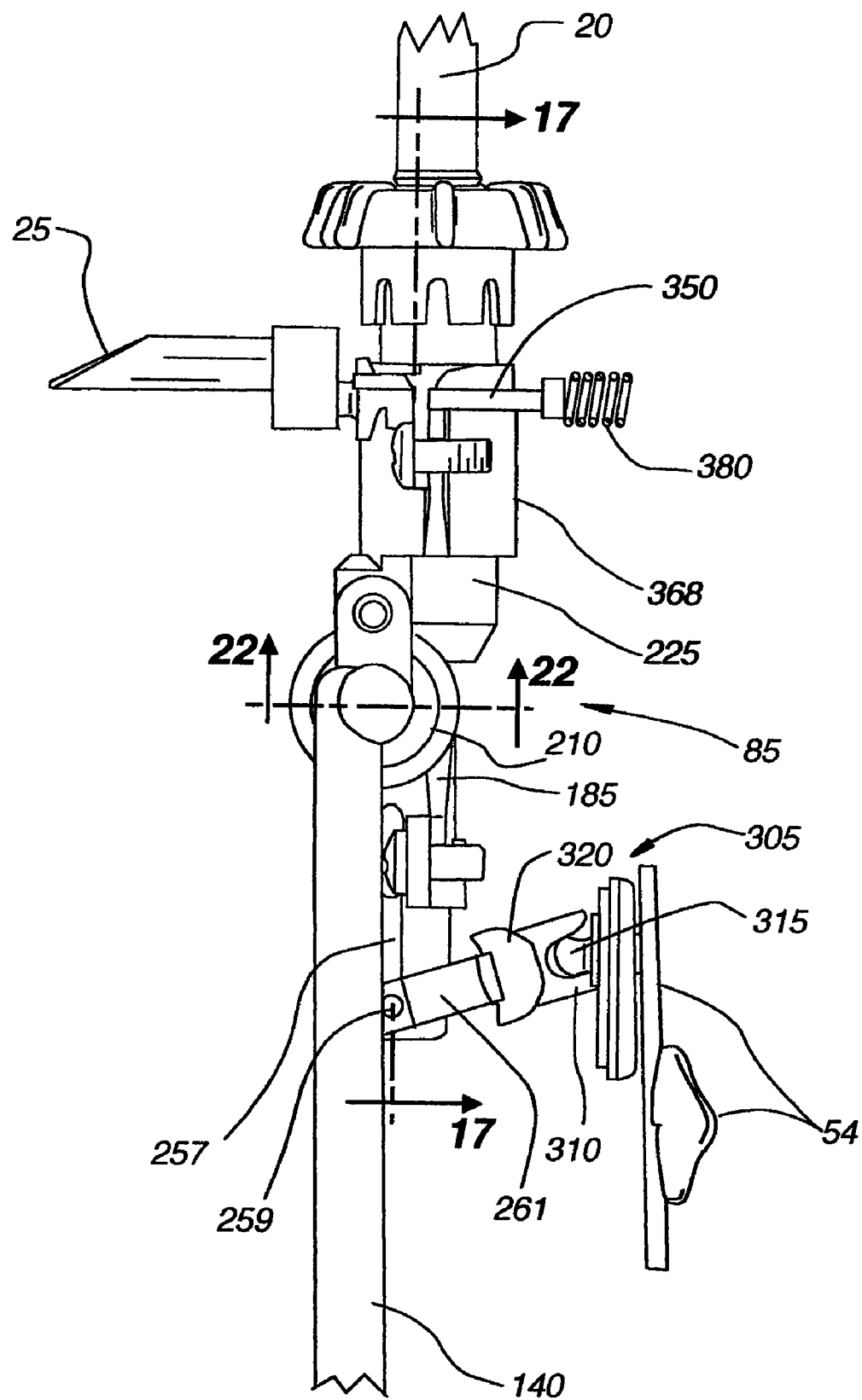
FIG. 15 is a side elevation of the same elements depicted in FIG. 14, as viewed from the same direction as FIG. 6.
Figure 16:
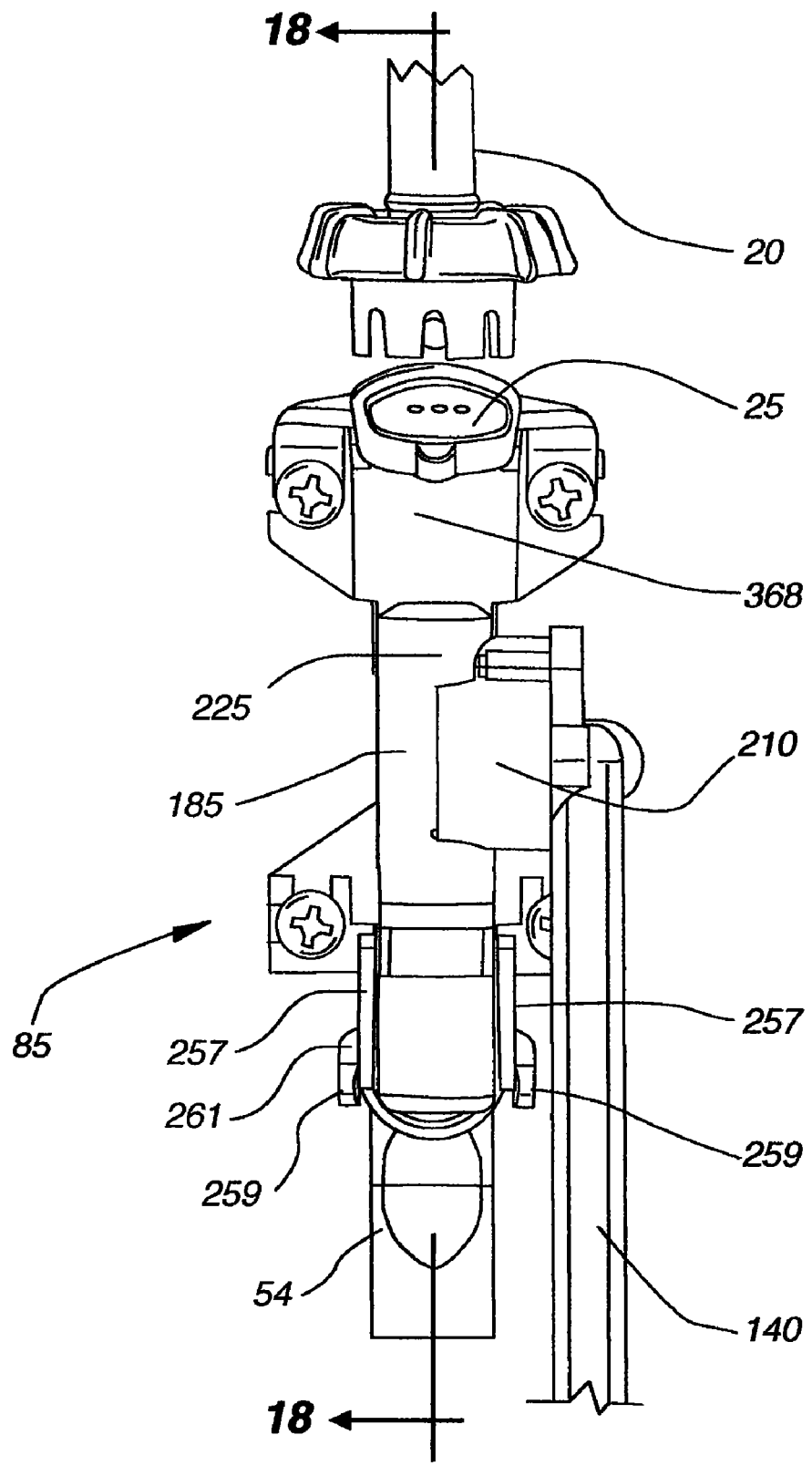
FIG. 16 is a side elevation of the same elements depicted in FIG. 14, as viewed from the same direction as FIG. 4.
Figure 17A:
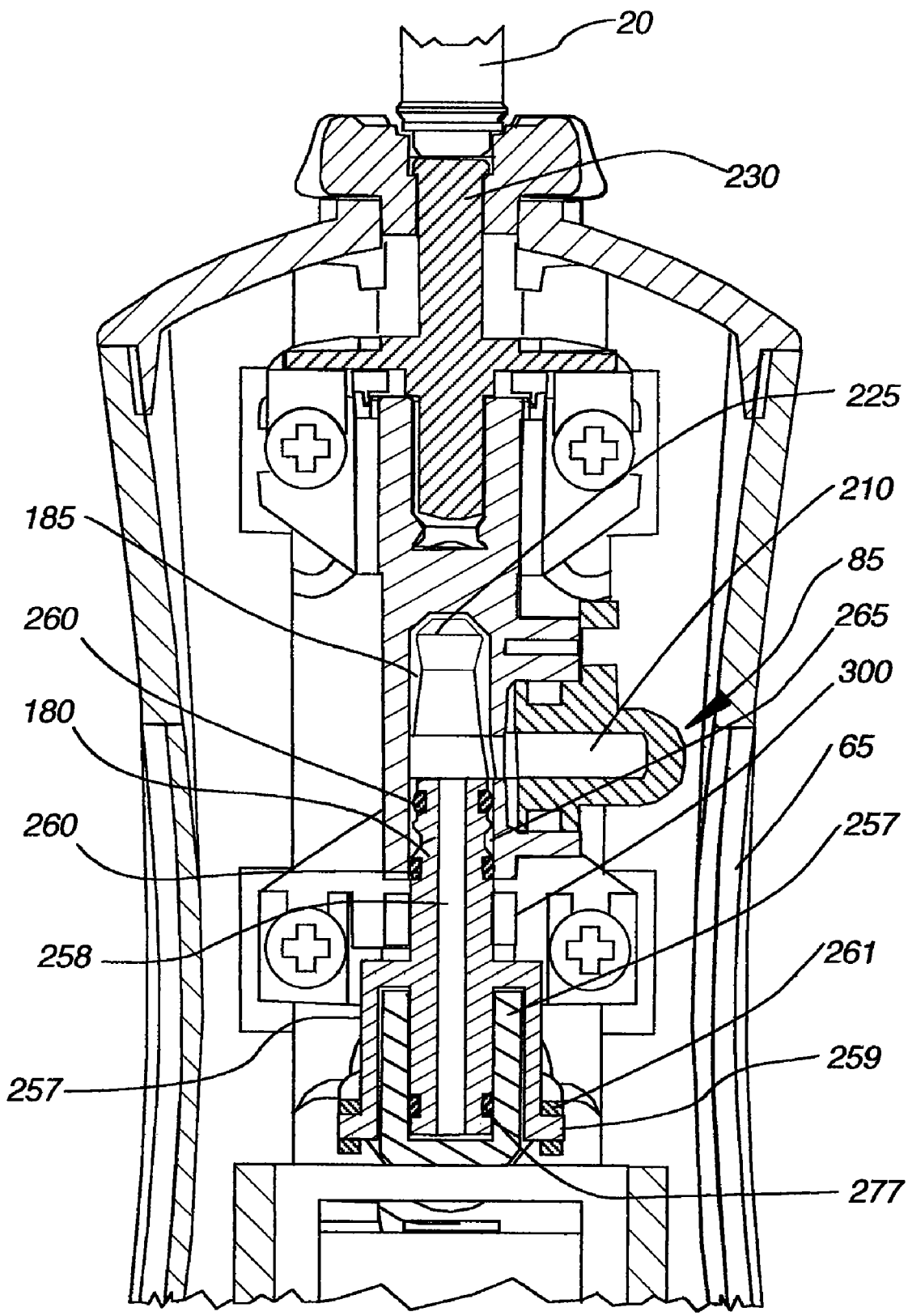
FIG. 17A is a longitudinal cross section of the pressure control valve assembly as taken along section line 17-17 in FIG. 15 and wherein a spool is in a rearward location (i.e., a high discharge pressure position) within the valve cylinder.
Figure 17B:
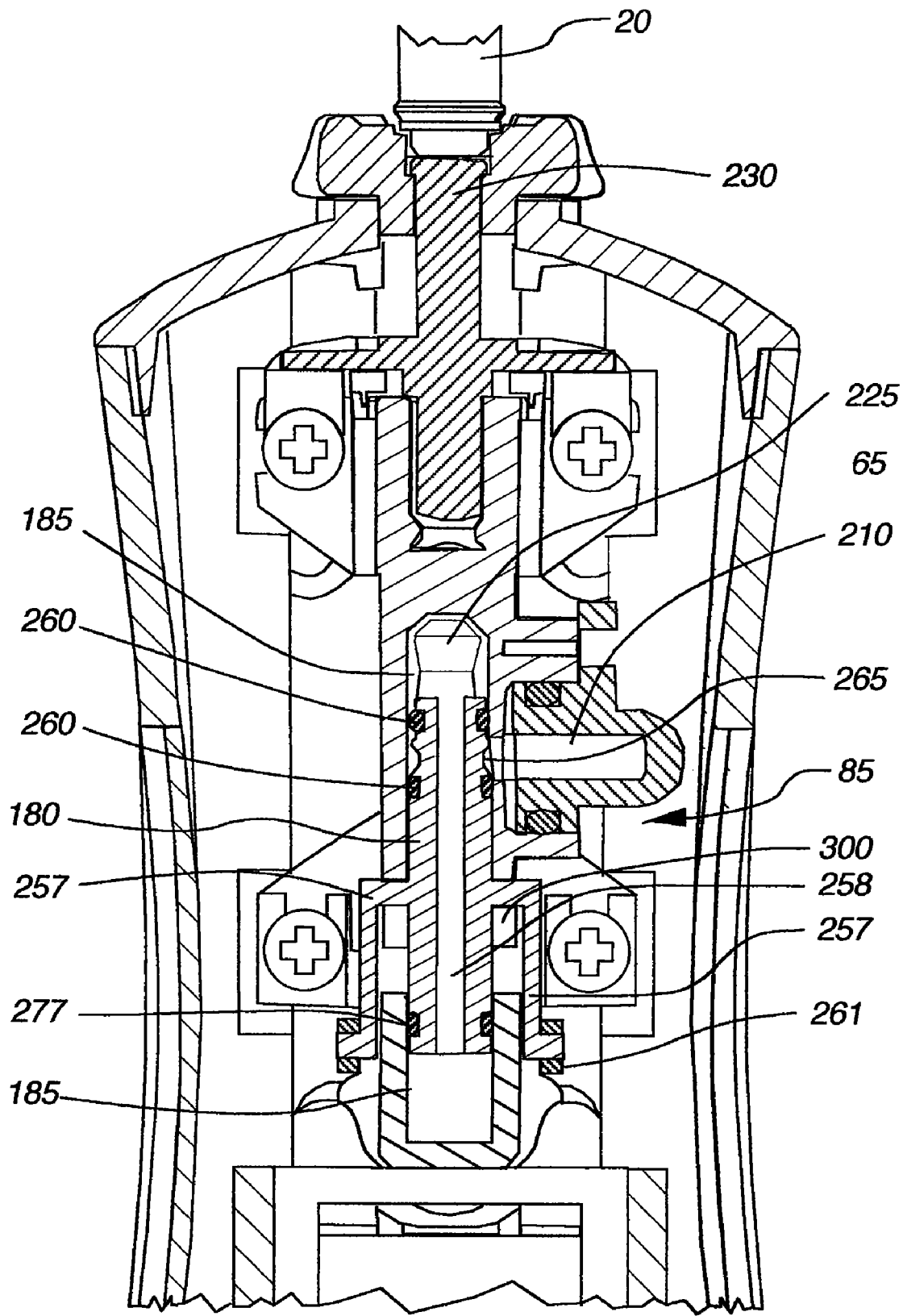
FIG. 17B is the same view depicted in FIG. 17A, except the spool is in a forward location (i.e., a low discharge pressure position) within the valve cylinder.
Figure 18A:
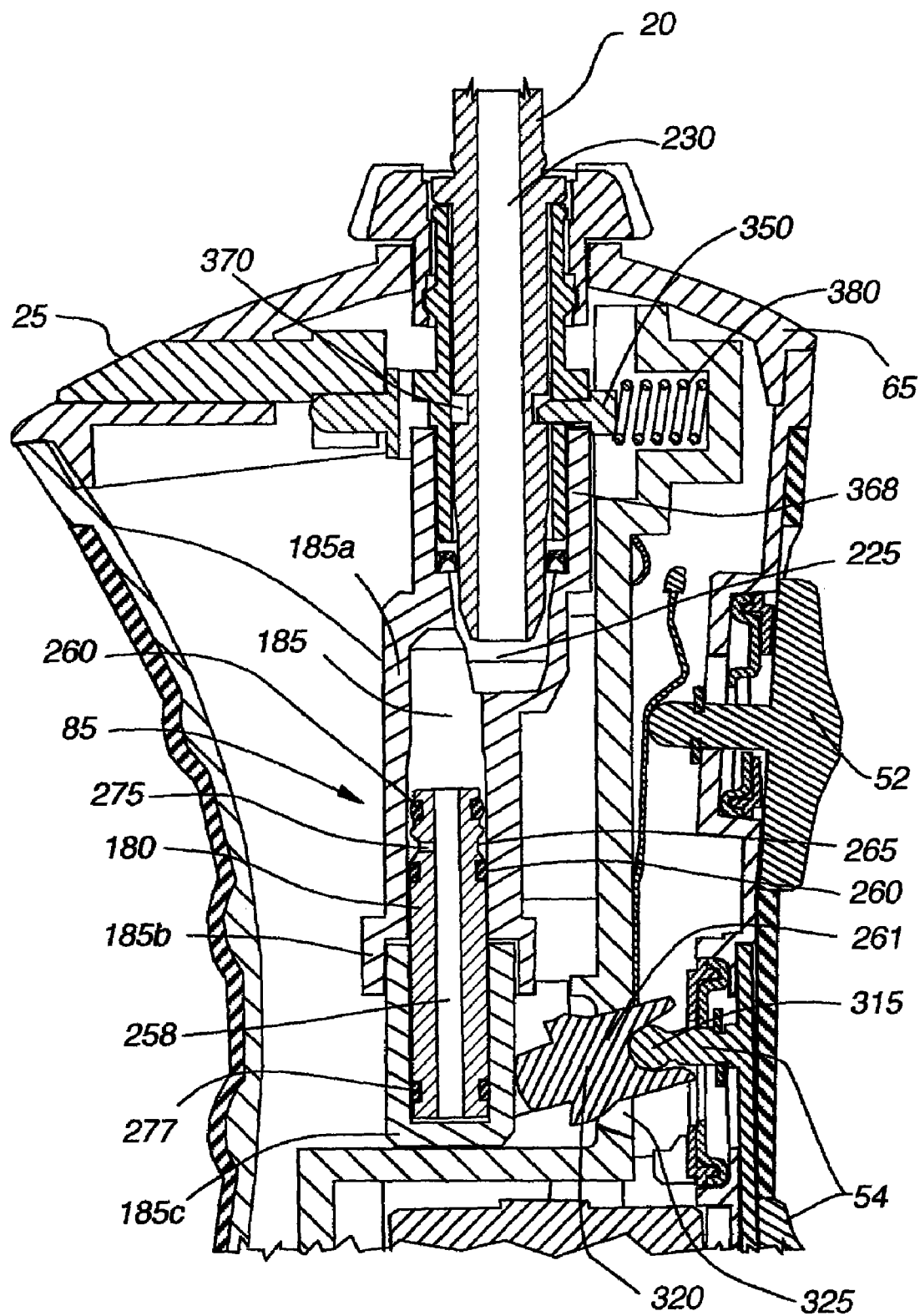
FIG. 18A is a longitudinal cross section of the pressure control valve assembly as taken along section line 18-18 in FIG. 16 and wherein the spool is in a rearward location (i.e., a high discharge pressure position) within the valve cylinder.
Figure 18B:
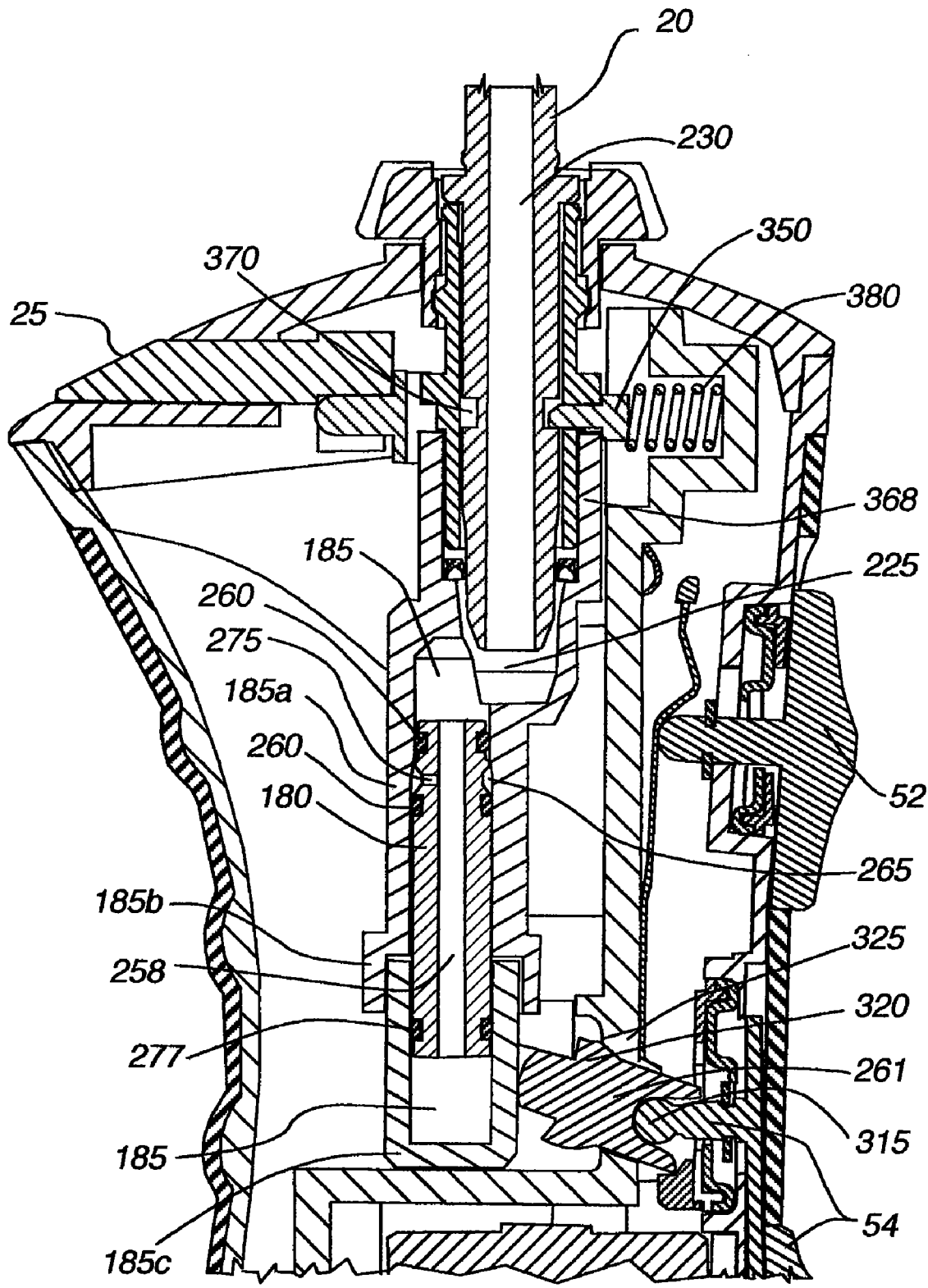
FIG. 18B is the same view depicted in FIG. 18A, except the spool is in a forward location (i.e., a low discharge pressure position) within the valve cylinder.
Figure 19:
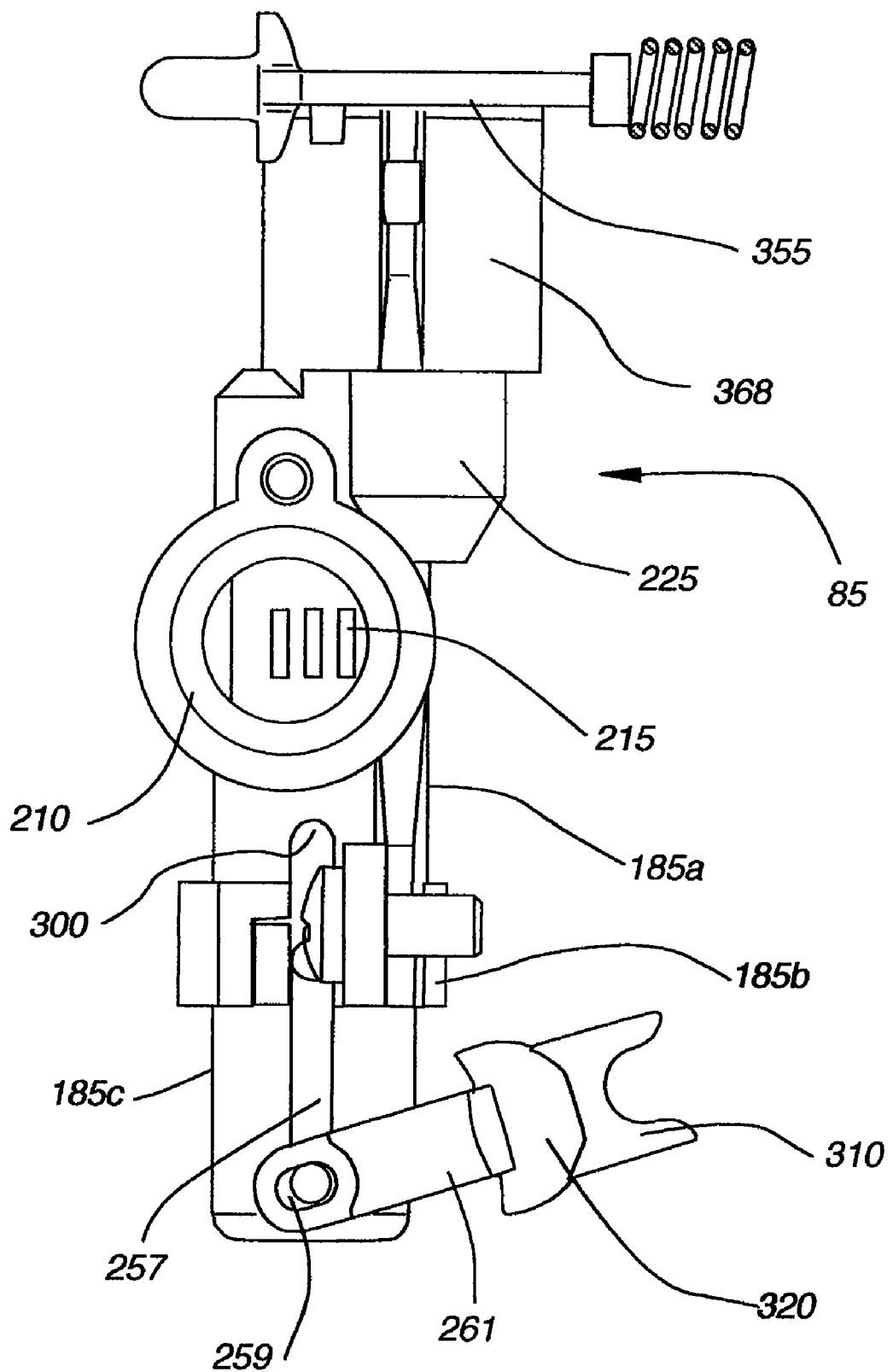
FIG. 19 is a side view of the pressure control valve assembly as shown in FIG. 15, except the discharge tube, nozzle and control button are hidden for clarity purposes.
Figure 20:
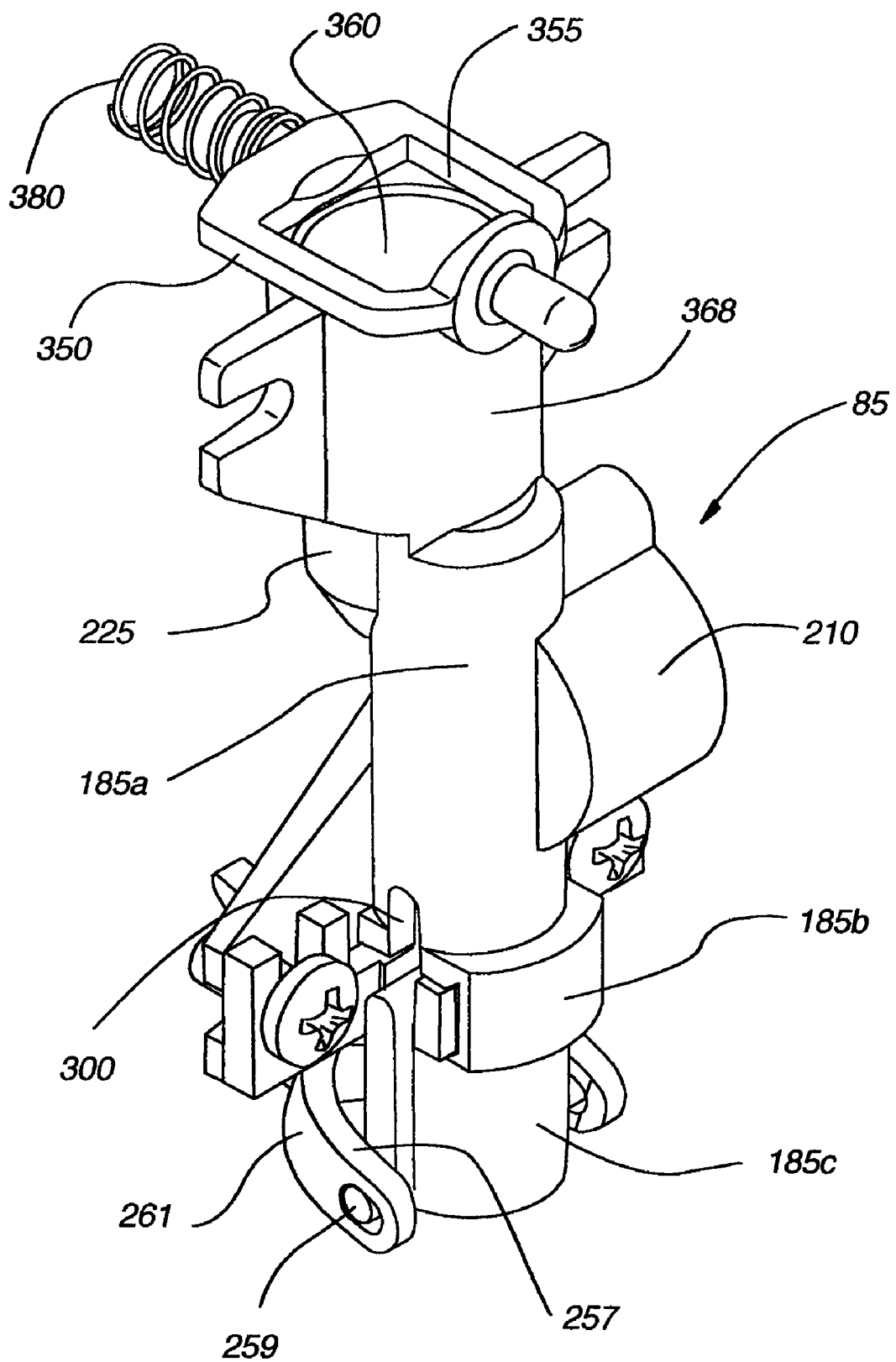
FIG. 20 is an isometric view of the valve assembly wherein the discharge tube, nozzle and control button are hidden for clarity purposes.
Figure 21:
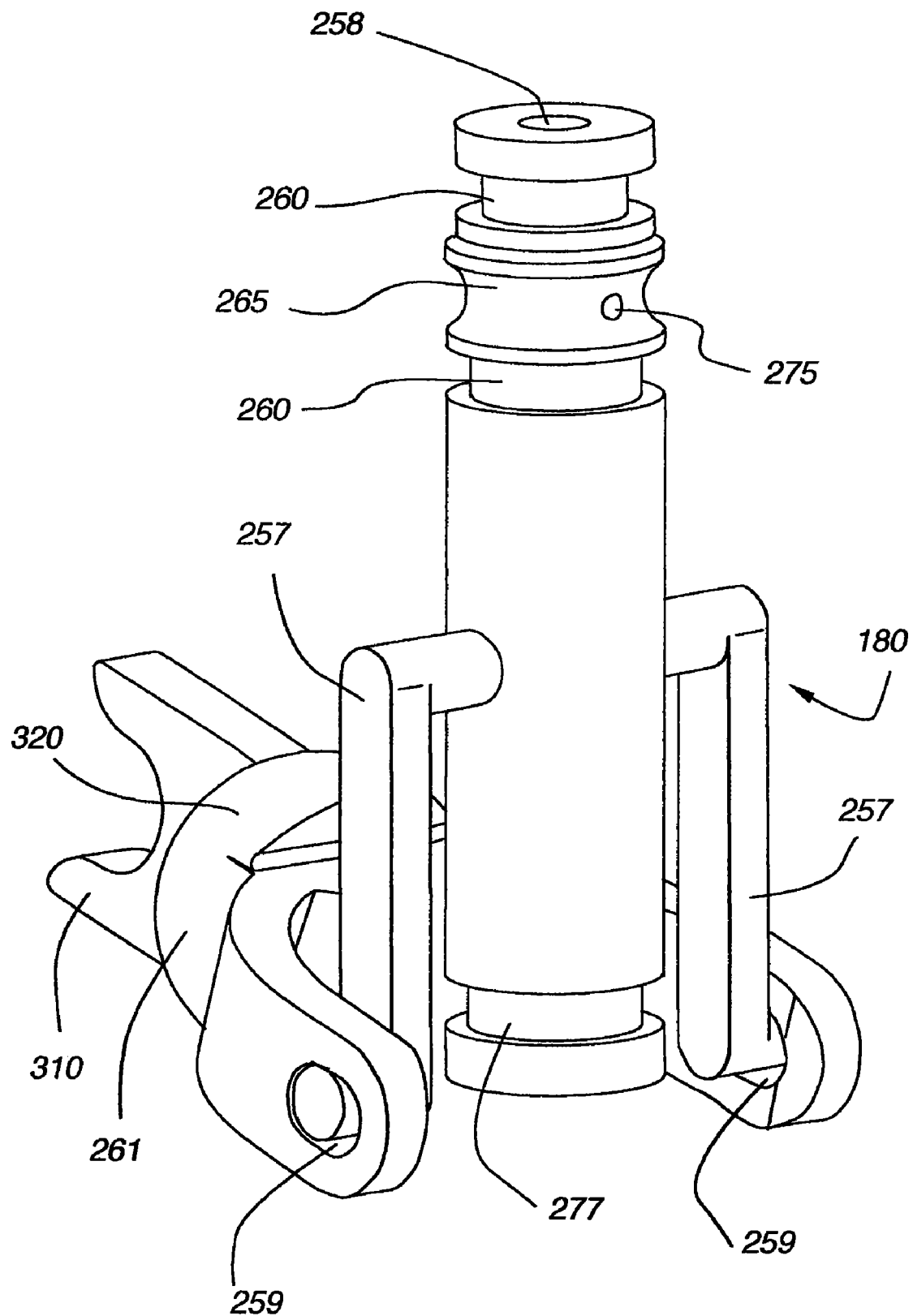
FIG. 21 is an isometric view of the spool and yoke.
Figure 22:
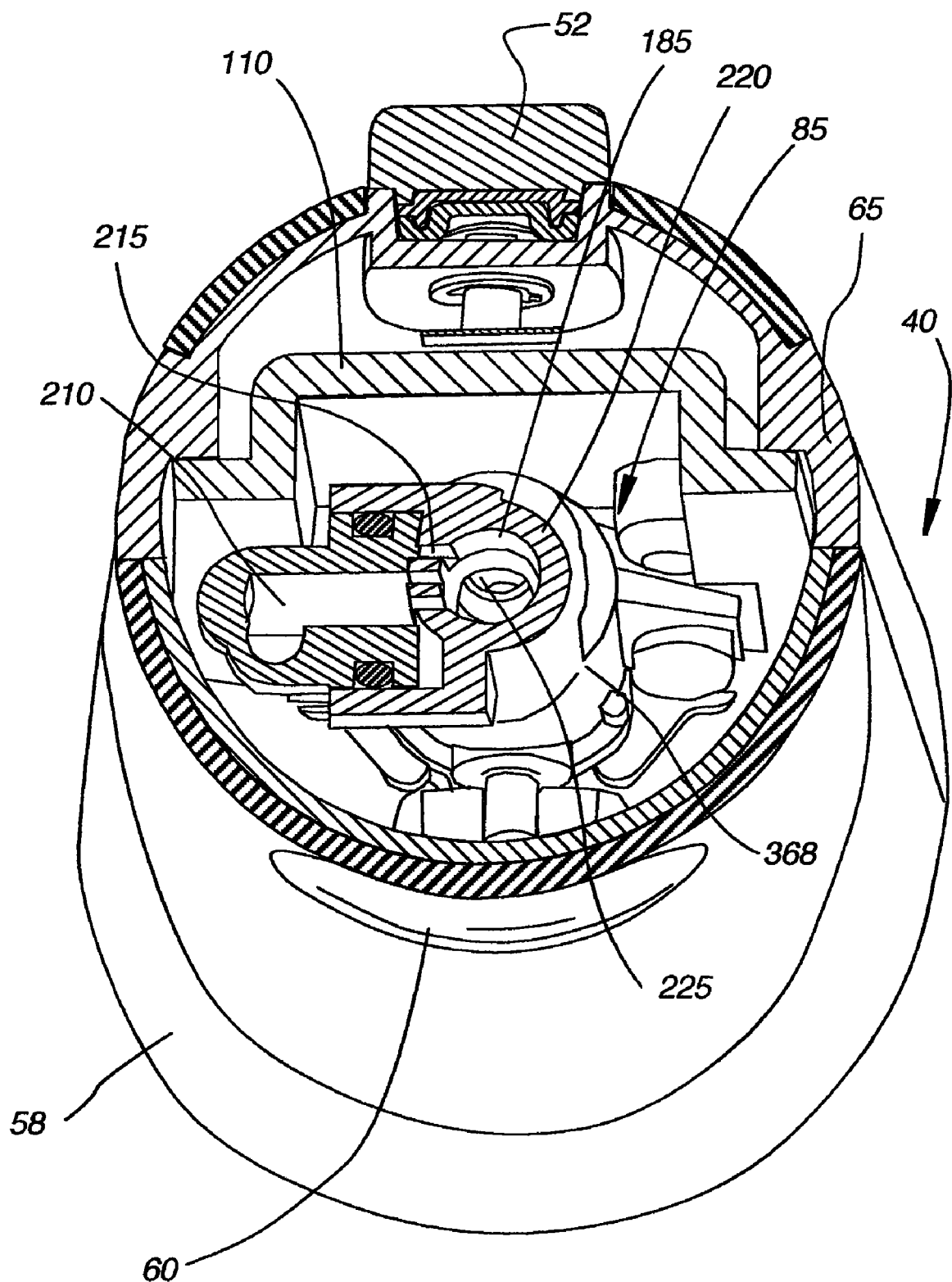
FIG. 22 is an isometric latitudinal cross section taken along section line 22-22 in FIG. 15.

For a discussion of the pressure control valve assembly 85, reference is made to FIGS. 14-22. FIG. 14 is an isometric view of the pressure control valve assembly 85 with the majority of the rest of the handheld oral irrigator 10 hidden for clarity purposes. FIG. 15 is a side elevation of the same elements depicted in FIG. 14, as viewed from the same direction as FIG. 6. FIG. 16 is a side elevation of the same elements depicted in FIG. 14, as viewed from the same direction as FIG. 4. FIG. 17A is a longitudinal cross section of the pressure control valve assembly 85 as taken along section line 17-17 in FIG. 15 and wherein a spool 180 is in a rearward location (i.e., a high discharge pressure position) within the valve cylinder 185. FIG. 17B is the same view depicted in FIG. 17A, except the spool 180 is in a forward location (i.e., a low discharge pressure position) within the valve cylinder 185. FIG. 18A is a longitudinal cross section of the pressure control valve assembly 85 as taken along section line 18-18 in FIG. 16 and wherein the spool 180 is in a rearward location (i.e., a high discharge pressure position) within the valve cylinder 185. FIG. 18B is the same view depicted in FIG. 18A, except the spool 180 is in a forward location (i.e., a low discharge pressure position) within the valve cylinder 185. FIG. 19 is a side view of the pressure control valve assembly 85 as shown in FIG. 15, except the discharge tube 140, nozzle 20 and control button 54 are hidden for clarity purposes. FIG. 20 is an isometric view of the pressure control valve assembly 85 wherein the discharge tube 140, nozzle 20 and control button 54 are hidden for clarity purposes. FIG. 21 is an isometric view of the spool 180 and yoke 190. FIG. 22 is an isometric latitudinal cross section taken along section line 22-22 in FIG. 15.

As can be understood from FIGS. 14-18B and 22, fluid pumped through the discharge tube 140 from the pump 75 enters an inlet 210 of the pressure control valve assembly 85. As depicted in FIG. 19 and FIG. 22, in one embodiment, to enter the valve cylinder 185, the fluid passes through slot openings 215 in the cylinder wall 220.

As can be understood from FIGS. 17A-18B, a spool 180 is located in the cylinder 185 and longitudinally displaceable within the cylinder 185. As illustrated in FIG. 21, the spool 180 is cylindrically shaped with a pair of arms 257 extending outwardly and rearwardly from a middle portion of the spool 180. A lumen 258 extends longitudinally through the length of the spool 180. The free ends of the arms 257 are received in pivot holes 259 in a yoke 261. The distal end of the spool 180 includes a pair of o-ring receiving grooves 260, a fluid groove 265 positioned between the o-ring grooves 260, and an orifice 275 extending between the fluid groove 265 and the lumen 270. The proximal end of the spool 180 includes an o-ring receiving groove 277.

As indicated in FIGS. 17A and 18A, when the spool 180 is located rearwardly in the cylinder 185, the fluid passes through the slot openings 215 (see FIGS. 19 and 20) and directly from the front of the cylinder 185, through the valve assembly outlet 225, through the lumen 230 of the nozzle 20, and out the distal tip of the nozzle 20 as a high discharge pressure fluid stream. As indicated in FIGS. 17B, 18B and 21, when the spool 180 is located forwardly in the cylinder 185, the fluid passes through the slot openings 215 (see FIGS. 19 and 20) and between the fluid groove 265 and the inner circumferential surface of the cylinder 185, through the orifice 275, into the lumen 258 of the spool 180, through the valve assembly outlet 225, through the lumen 230 of the nozzle 20, and out the distal tip of the nozzle 20 as a low discharge pressure fluid stream.

As can be understood from FIGS. 17A-20, when the spool 180 is in the forward position within the cylinder 185 (i.e., the low discharge pressure position), the fluid flow passing through the pressure control valve assembly 85 must overcome a substantially increased frictional resistance as compared to when the spool 180 is in the rearward position within the cylinder 185 (i.e., the high discharge pressure position). Accordingly, when the spool 180 is in the low discharge pressure position, the pressure control valve assembly 85 creates a substantially high-pressure drop in the fluid flow passing through the assembly 85 as compared to when the spool 180 is in the high discharge pressure position. Thus, without having to adjust the operating speed of the pump 75, a user may adjust the discharge pressure of a fluid stream emanating from the nozzle 20 of the oral irrigator 10 by adjusting the position of the spool 180 within the cylinder 185. Accordingly, the discharge pressure may be substantially modified by a user without causing a substantial change in the preferred pulse rate of the fluid stream.

As can be understood from FIGS. 17A-20, moving the spool 180 from the high discharge pressure position (see FIGS. 17A and 18A) to the low discharge pressure position (see FIGS. 17B and 18B) modifies, in several ways, the fluid flow path through the discharge pressure control assembly 85 and, as a result, the fluid flow path between the pump 75 and the nozzle 20. First, moving the spool 180 from the high to the low discharge pressure position increases the length of the fluid flow path because the flow is diverted about the fluid groove 265, through the orifice 275 and through the lumen 258 before the flow can pass through the cylinder outlet 225 to the nozzle 20. Second, moving the spool 180 from the high to the low discharge pressure position substantially decreases the diameters or flow areas of the fluid flow path because the diameters or flow areas of the fluid groove 265, orifice 275, and lumen 258 are substantially smaller than the internal diameter or flow area of the cylinder 185. Third moving the spool 180 from the high to the low discharge pressure position increases the number of direction deviations the fluid flow must undergo because the fluid must travel a tortuous route around the groove 265 and through the orifice 275 and lumen 258 before the flow can pass through the cylinder outlet 225 to the nozzle 20.

Each of these modifications to the fluid flow path brought about by moving the spool 180 from the high to low discharge pressure position increases the magnitude of the fluid flow friction between the pump 75 and the nozzle 20. Accordingly, although the pump 75 continues to operate at generally the same speed and provides a fluid stream at generally the same pulse rate, because the spool 180 moves from the high to the low discharge pressure position within the cylinder 185, the discharge pressure of the fluid stream at the distal end of the nozzle 20 decreases from a high to low discharge pressure.

Research has indicated that some fluid stream pulse rates are more effective than other pulse rates. For example, in one embodiment of the subject invention, the pump 75 of the oral irrigator 10 cycles at a rate such that it discharges a fluid stream out the nozzle 20 that has a pulse rate of 1000-1600 pulses per minute and, in one embodiment, 1100-1400 pulses per minute and, in one embodiment, 1200 pulses per minute. As discussed in U.S. Pat. No. 3,227,158 issued to Mattingly, which is incorporated by reference herein in its entirety, a pulse rate of 1000-1600 pulses per minute has been found to be the most effective pulse rates for the purposes of oral hygiene and health. Other highly effective pulse rates for the purposes of oral hygiene and health also include 1100-1400 pulse per minute and 1200 pulses per minute.

The pressure control feature of the subject invention is advantageous because it allows a user to adjust the fluid stream discharge pressure to suit the user's comfort preferences while maintaining the pulse rate generally at a preferred pulse rate. For example, regardless of whether the pressure control valve assembly 85 is set to cause a low or high discharge pressure fluid stream to emanate from the nozzle 20, the fluid stream will have a preferred number of pulses per minute (e.g., 1000-1600 pulses per minute, 1100-1400 pulses per minute, 1200 pulses per minute, etc.).

For a discussion of the cylinder's configuration, reference is again made to FIGS. 14 and 17A-20. As best understood from FIGS. 14, 19 and 20, the cylinder 185 of the pressure control valve assembly 185 includes a proximal portion 185*a* received within a collar portion 185*b* of a distal portion 185*c*. A slot 300 extends longitudinally along the sides of the cylinder 185, and the arms 257 of the spool 180 extend through the slots 300 to couple with the arms of the yoke 261. As indicated in FIGS. 17A-18B, the cylinder 185 is hollow to receive the spool 180, and the proximal end of the cylinder proximal portion 185*c* is walled-off such that when a fluid flows into the lumen 258 of the spool 180, the fluid impacts the proximal end of the cylinder proximal portion 185*c* to establish a back pressure condition within the pressure control valve assembly 85. As can be understood from FIGS. 17A and 17B, the o-rings 260,277 prevent fluid from escaping the cylinder 185 through the slots 300.

For a discussion of the linkage 305 used to cause the spool 180 to displace within the cylinder 185, reference is again made to FIGS. 9, 14, 15, 18A-21. As best understood from these figures, the linkage 305 includes the yoke 261 and the pressure control 54. The yoke 261 includes a pair of arms, and each arm has a pivot hole 259 near its free end. The pivot holes 259 pivotally receive therein the free ends of the spool arms 257. The yoke includes an arcuately slotted tongue 310 opposite the yoke arms for pivotally receiving therein a ball 315 extending from the pressure control 54.

As indicated in FIG. 9, in one embodiment, the pressure control 54 is a slide supported by the housing 65 of the handle portion 15 of the irrigator 10. As illustrated in FIGS. 19 and 21, the yoke 261 has a rocker portion 320 from which the tongue 310 extends. As shown in FIGS. 18A and 18B, the rocker portion 320 resides within a hole or slot 325 in the chassis plate 110, which allows the tongue 310 to rock towards the nozzle 20 or towards the base 30, depending on how the slide 54 is displaced along the housing 65.

As indicated in FIG. 18A, when the slide 54 is shifted towards the nozzle 20, the tongue 310 is rocked towards the nozzle 20 thereby causing the yoke 261 to pivot about the hole 325 in the chassis plate 110 such that the yoke arms move towards the base 30 and pull the spool arms 257 towards the base 30, which causes the spool 180 to move towards the base 30 (i.e., the spool 180 moves into the high discharge pressure position). As indicated in FIG. 18B, when the slide 54 is shifted towards the base 30, the tongue 310 is rocked towards the base 30 thereby causing the yoke 261 to pivot about the hole 325 in the chassis plate 110 such that the yoke arms move towards the nozzle 20 and pull the spool arms 257 towards the nozzle 20, which causes the spool 180 to move towards the nozzle 20 (i.e., the spool 180 moves into the low discharge pressure positions).

For a discussion regarding the elements of the nozzle release, reference is again made to FIGS. 9, 14, 15 and 18A-20. As illustrated in these figures, the nozzle release button 25 is coupled to a collar 350 having an opening 355 centered about the hole 360 of the nozzle base receiving cylinder 368, which extends from the cylinder outlet 225. The proximal end of the nozzle 20 is received in the receiving cylinder 368 and the collar 350. The collar 350 is biased into a nozzle base groove 370 by a spring 380. The groove 370 extends about the circumference of the nozzle base. To release or disengage the collar 350 from the nozzle base groove 370 to allow the nozzle 20 to be withdrawn from the receiving cylinder 368, the nozzle release button 25 is depressed against the biasing force of the spring 380, which causes the collar 350 to shift out of engagement with the groove 370. The nozzle 20 is then withdrawn from the cylinder 368.

As can be understood from the preceding discussion, the oral irrigator of the present invention is advantageous because it allows a user to adjust the discharge pressure of the fluid stream emanating from the oral irrigator without bringing about a significant change in the pulse rate of the fluid stream. Thus, the oral irrigator can continue to supply a fluid stream at a preferred pulse rate regardless of the discharge pressure selected by the user.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. A handheld oral irrigator comprising:
   a fluid reservoir;
   a pump including a suction side and a discharge side, wherein the suction side is in fluid communication with the fluid reservoir;
   a pressure control assembly including a valve cylinder and a member longitudinally displaceable within the valve cylinder, wherein the valve cylinder has an inlet and an outlet, wherein the inlet is in fluid communication with the discharge side of the pump, and wherein the member includes a lumen and an orifice leading to the lumen from an outside surface of the member; and
   a nozzle in fluid communication with the outlet of the valve cylinder,
   wherein placing the member in a first position within the valve cylinder causes the orifice to be placed in fluid communication with the inlet and thereby define a fluid pathway from the inlet to the outlet that extends through the lumen,
   wherein placing the member in a second position within the valve cylinder isolates the orifice from the inlet and thereby defines a fluid pathway from the inlet to the outlet that does not extend through the lumen.

2. The oral irrigator of claim 1, wherein the member further includes a groove defined in the outside surface of the member, the orifice being located in the groove.

3. The oral irrigator of claim 1, further comprising an actuator for displacing the member within the valve cylinder and wherein the member comprises a portion that extends through the valve cylinder to couple to the actuator.

4. The oral irrigator of claim 3, wherein the portion of the member is an arm that extends through a longitudinally extending slot in the valve cylinder, and the member is longitudinally displaceable within the valve cylinder.

5. The oral irrigator of claim 1, wherein the first position is proximal to the second position.

6. An oral irrigator comprising:
   a pump having a generally constant operating speed;
   a discharge nozzle fed by the pump; and
   a pressure control located between the pump and the discharge nozzle and including a valve cylinder defining an inlet in fluid communication with the pump and an outlet in fluid communication with the discharge nozzle and a spool axially displaceable within the valve cylinder between a first location and a second location,
   wherein when the spool is in the first location, a first resulting fluid pathway extending through the valve cylinder between the inlet and the outlet is caused to extend through the spool, and
   wherein when the spool is in the second location, a second resulting fluid pathway through the valve cylinder between the inlet and outlet has a route that is one or more of shorter in length, wider in diameter, or fewer in number of direction changes than a route of the first resulting fluid pathway.

7. The oral irrigator of claim 6, wherein the spool includes an axially extending lumen, the lumen forming at least a part of the first resulting fluid pathway.

8. The oral irrigator of claim 7, wherein the spool further includes an orifice extending from an outside surface of the spool to the lumen, the orifice forming at least a part of the first resulting fluid.

9. The oral irrigator of claim 7, wherein the spool further includes a groove defined in the outside surface of the spool, the orifice being located in the groove, the groove forming at least a part of the first resulting fluid pathway.

10. The oral irrigator of claim 6, wherein the second resulting fluid pathway does not extend through the spool.

11. An oral irrigator comprising:
    a pump for supplying a nozzle; and
    a pressure adjustment assembly including a valve cylinder and a spool displaceable within the valve cylinder, the valve cylinder including an inner surface, an inlet opening defined the inner surface and in fluid communication with the pump, and an outlet in fluid communication with the nozzle, the spool including an outer surface, a lumen and an orifice extending between the outer surface and the lumen,
    wherein, when the spool is located in a first position within the valve cylinder, a first resulting fluid flow pathway extends through the cylinder between the inlet and outlet via the orifice and lumen, and
    wherein, when the spool is located in a second position with the valve cylinder, a second resulting fluid flow pathway through the cylinder between the inlet and outlet does not include the orifice and lumen.

12. The oral irrigator of claim 11, wherein the spool includes a groove defined in the outer surface and the first resulting fluid flow pathway extends through the cylinder between the inlet and outlet via groove.

13. The oral irrigator of claim 12, wherein the first fluid flow pathway is at least partially in existence between the groove and the inner surface.

14. The oral irrigator of claim 12, wherein the orifice is located in the groove.

15. The oral irrigator of claim 12, wherein the orifice is located on an opposite side of the spool from the inlet, the groove providing fluid communication between the inlet and the orifice when the spool is in the first position.

16. The oral irrigator of claim 11, wherein the lumen extends axially through the spool.

17. The oral irrigator of claim 11, wherein the lumen daylights at opposite ends of the spool.

18. The oral irrigator of claim 11, wherein inner surface and the outer surface are both generally cylindrical in shape.

19. The oral irrigator of claim 18, wherein the spool further includes a groove defined in the outer surface and in fluid communication with the lumen via the orifice.

20. The oral irrigator of claim 19, wherein the groove extends generally transverse to a longitudinal axis of the spool.

21. An oral irrigator comprising:
    a pump for supplying a nozzle; and
    a pressure adjustment assembly comprising a valve cylinder and a spool longitudinally displaceable within the valve cylinder, wherein the spool in a distal position within the valve cylinder causes a fluid flow pathway between an inlet and an outlet of the valve cylinder extending through the valve cylinder to extend through at least a portion of the spool and the spool in a proximal position within the valve cylinder causes the fluid flow pathway between the inlet and the outlet extending through the valve cylinder to not extend through the spool.

* * * * *